United States Patent [19]
Takeda et al.

[11] Patent Number: 4,874,898
[45] Date of Patent: Oct. 17, 1989

[54] NOVEL SUBSTITUTED ANTHRASTEROID DERIVATIVES

[75] Inventors: Ken'ichi Takeda, Hyogo; Isao Horibe, Osaka, both of Japan

[73] Assignee: Shionogi and Co., Ltd. Patent Department, Osaka, Japan

[21] Appl. No.: 216,525

[22] Filed: Jul. 7, 1988

[30] Foreign Application Priority Data

Jul. 31, 1987 [JP] Japan .................. 62-193608

[51] Int. Cl.$^4$ ............................................. C07C 49/617
[52] U.S. Cl. ................................... 568/369; 549/432; 558/260; 560/194
[58] Field of Search ........................ 568/369; 549/432; 558/260

[56] References Cited

FOREIGN PATENT DOCUMENTS 249257 9/1987 Fed. Rep. of Germany ...... 568/369
1268241 3/1972 United Kingdom ................ 568/369

OTHER PUBLICATIONS

Tetrahedron, vol. 31, 1975, pp. 2237–2242, Pergamon Press, Oxfor, GB; J. C. Jacquesy et al.
Chemical Abstracts, vol. 72, 1970, pp. 368–369, no. 12953n, Columbus, Ohio, US; D. K. Banarjee et al.
Tetrahedron Letters, no. 23, 1968, pp. 2771–2775, Pergamon Press, Oxford, GB; D. K. Banerjee et al.

Primary Examiner—James H. Reamer
Attorney, Agent, or Firm—Wenderoth, Lind & Ponack

[57] ABSTRACT

Substituted anthrasteroid derivatives represented by the following formula:

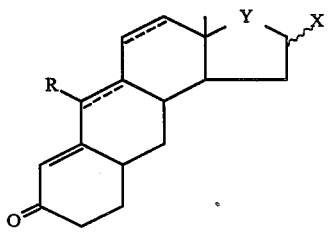

wherein R is hydrogen or lower alkyl; X is hydrogen, lower alkyl, halogen, hydroxy, hydroxymethyl, or halomethyl; Y is C=O, CH~OR', or OH C R", wherein R' is hydrogen, lower alkyl, cycloalkyl which may have an unsaturated bond or a substituent, or aliphatic lower acyl which may have carboxy or its lower alkyl ester at the terminal; R" is lower alkyl or lower alkynyl; the dotted line indicates the presence or absence of double bond; and the wavy line indicates α or β configuration; or ketal derivatives thereof being effective against androgen-dependent diseases e.g., prostatic hypertrophy, prostatic cancer.

7 Claims, No Drawings

NOVEL SUBSTITUTED ANTHRASTEROID DERIVATIVES

BACKGROUND OF THE INVENTION (1) Field of the Invention

The invention relates to novel anthrasteroid derivatives represented by the following general formula (I) which are effective against androgen-dependent diseases especially against prostatic hypertrophy, prostatic cancer and so forth.

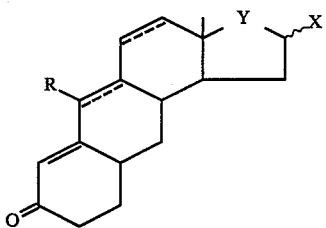

wherein R is hydrogen or lower alkyl; X is hydrogen, lower alkyl, halogen, hydroxy, hydroxymethyl, or halomethyl; Y is C=O, CH~OR', or OH—CR", wherein R' is hydrogen, lower alkyl, cycloalkyl which may have an unsaturated bond or a substituent, or aliphatic lower acyl which may have carboxy or its lower alkyl ester at the terminal; R" is lower alkyl or lower alkynyl; the dotted line indicates the presence or absence of double bond; and the wavy line indicates an α or β configuration.

(2) Description of the Prior Art

In the treatment of androgen dependent-diseases, it is general to use a steroid hormone type medicine i.e. anti-androgen. As a well-known commercially available anti-androgen, cyproterone acetate, chlormadinone acetate, oxendolone or the like is exemplified.

As all of the above-mentioned commercially available antiandrogens have a normal steroid structure, the separation of antiandrogenicity from the native effects of steroid hormones is not sufficient. Occurrence of various side effects such as hypersensitiveness, gain of weight, gynecomastia, adrenal medullary insufficiency, feeling of fatigue, cephalalgia, feeling of lassitude, oligocythemia, pyrexia, loss of sexuality and so forth has been observed, accordingly.

SUMMARY

A substituted anthrasteroid derivative represented by the following formula:

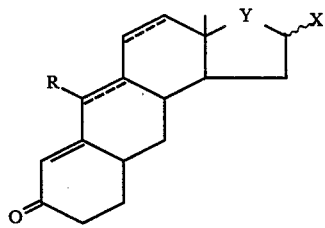

wherein R is hydrogen or lower alkyl; X is hydrogen, lower alkyl, halogen, hydroxy, hydroxymethyl, or halomethyl; Y is C=O, CH~OR', or OH—CR", wherein R' is hydrogen, lower alkyl, cycloalkyl which may have an unsaturated bond or a substituent, or aliphatic lower acyl which may have carboxy or its lower alkyl ester at the terminal; R" is lower alkyl or lower alkynyl; the dotted line indicates the presence or absence of a double bond; and the wavy line indicates an α or a β configuration; or ketal derivative thereof. Said compounds which have antiandrogenic activity are effective against androgen-dependent diseases.

DESCRIPTION OF THE PREFERRED EMBODIMENT

The present inventors who were interested in these problems investigated in order to separate the main effects sufficiently from the side effects. As a result, they have found that the aim is attained by altering a basic steroid structure into an anthracene form.

The aimed compounds of the present invention are represented by the above general formula (I) and these compounds potently inhibit the hypertrophy of prostate and seminal vesicle and also potently inhibit the growth of an androgen-dependent tumor.

In the definition of the above-mentioned general formula, the lower alkyl represented by R refers to a straight or branched alkyl of 1 to 5 carbon atoms, e.g., methyl, ethyl, propyl, isopropyl, butyl, isobutyl, pentyl, s-pentyl.

The definition of lower alkyl represented by X is the same as defined in R. The halogen atom refers to F, Cl, or Br and the halomethyl refers to fluoromethyl, chloromethyl, or bromomethyl. The definition of lower alkyl represented by R' is also the same as defined in R. The cycloalkyl which may have an unsaturated bond or substituents refers to a 5 to 10-membered ring, e.g., 1-cyclopentenyl, 1-cyclohexenyl, 1-cycloheptenyl, 1-cyclooctenyl, 1-cyclodecanyl, 1-methoxycyclopentyl, 1-ethoxycyclopentyl, 1-ethoxycyclohexenyl, 1-methoxycycloheptyl. The aliphatic lower acyl which may have carboxy or its lower alkyl ester at the other end refers to aliphatic lower acyl derived from aliphatic carboxylic acid of 1 to 6 carbon atoms, (e.g., formic acid, acetic acid, propionic acid, butyric acid pentanoic acid, hexanoic acid) or dibasic carboxylic acid of 3 to 10 carbon atoms (e.g., malonic acid, succinic acid, glutaric acid, adipic acid, pimelic acid, suberic acid, azelaic acid, sebacic acid) in which the one end forms an ester linkage with the 3-hydroxy of cyclopenta[a]anthracene and the other end remains as carboxy or the carboxy of the other end is esterified with lower alkyl such as methyl, ethyl, or propyl. The definition of lower alkyl represented by R" is the same as that of R. The lower alkynyl represented by R refers to the alkynyl of 2 to 4 carbon atoms, e.g., ethynyl, propargyl, 3-butyn-1-yl.

Illustrative of the compounds (I) of the present invention are as follows:

3β-hydroxy-3aβ,6α-dimethyl-2,3,3a,4,5,5aα,6,8,9,10,-10aβ,11,11aβ,11bα-tetradecahydro-1H-cyclopenta[a]anthracen-8-one, 3β-hydroxy-3aβ-methyl-2,3,3a,4,5,5aα,6,8,9,10,-10aβ,11,11aβ,11bα-tetradecahydro-1H-cyclopenta[a]anthracen-8-one, 3β-hydroxy-3aβ,6-dimethyl-2,3,3a,4,5,8,9,10,10aβ,11,-11aβ,11bα-dodecahydro-1H-cyclopenta[a]anthracen-8-one, 3β-hydroxy-3aβ,6-dimethyl-2,3,3a,8,9,10,10aβ,11,-11aβ,11bα-decahydro-1H-cyclopenta[a]anthracen-8-one, 3β-hydroxy-3aβ-methyl-2,3,3a,8,9,10,10aβ,11,11aβ,11bα-decahydro-1H-cyclopenta[a]anthracen-8-one, 3aβ,6-dimethyl-2,3,3a,4,5,8,9,10,10aβ,11,11aβ,11bα-dodecahydro-1H-cyclopenta[a]anthracene-3,8-dione, 3aβ,6-dimethyl-3β-(3-carboxypropionyloxy)-2,3,3a,4,5,8,9,10,10aβ,11,11aβ,11bα-dodecahydro-1H-cyclopenta[a]anthracen-8-one, 3β-methoxy-3aβ,6-dimethyl-2,3,3a,4,5,8,9,10,10aβ,11,11aβ,11bα-dodecahydro-1H-cyclopenta[a]anthracen-8-one, 3β-(1-methoxycyclopentyloxy)-3aβ,6-dimethyl-2,3,3a,4,5,8,9,10,10aβ,11,11aβ,11bα-dodecahydro-1H-cyclopenta[a]anthracen-8-one, 3β-(1-cyclopentenyloxy)-3aβ,6-dimethyl-2,3,3a,4,5,8,9,10,10aβ,11,11aβ,11bα-dodecahydro-1H-cyclopenta[a]anthracen-8-one, 3β-hydroxy-3α,3aβ,6-trimethyl-2,3,3a,4,5,8,9,10,10aβ,11,11aβ,11bα-dodecahydro-1H-cyclopenta[a]anthracen-8-one, 3α-ethynyl-3β-hydroxy-3aβ,6-dimethyl-2,3,3a,4,5,8,9,10,10aβ,11,11aβ,11bα-dodecahydro-1H-cyclopenta[a]anthracen-8-one, 3β-hydroxy-2β-hydroxymethyl-3aβ,6-dimethyl-2,3,3a,4,5,8,9,10,10aβ,11,11aβ,11bα-dodecahydro-1H-cyclopenta[a]anthracen-8-one, 3β-hydroxy-2α-hydroxymethyl-3aβ,6-dimethyl-2,3,3a,4,5,8,9,10,10aβ,11,11aβ,11bα-dodecahydro-1H-cyclopenta[a]anthracen-8-one, 2α-bromomethyl-3β-hydroxy-3aβ,6-dimethyl-2,3,3a,4,5,8,9,10,10aβ,11,11aβ,11bα-dodecahydro-1H-cyclopenta[a]anthracen-8-one, 2β-ethyl-3aβ,6-dimethyl-2,3,3a,4,5,8,9,10,10aβ,11,11aβ,11bα-dodecahydro-1H-cyclopenta[a]anthracen-3,8-dione, 2α-bromo-3aβ,6-dimethyl-2,3,3a,4,5,8,9,10,10aβ,11,11aβ,11bα-dodecahydro-1H-cyclopenta[a]anthracen-3,8-dione, 2β-bromo-3aβ,6-dimethyl-2,3,3a,4,5,8,9,10,10aβ,11,11aβ,11bα-dodecahydro-1H-cyclopenta[a]anthracen-3,8-dione, 2α-hydroxy-3aβ,6-dimethyl-2,3,3a,4,5,8,9,10,10aβ,11,11aβ,11bα-dodecahydro-1H-cyclopenta[a]anthracen-3,8-dione, 2β-fluoro-3aβ,6-dimethyl-2,3,3a,4,5,8,9,10,10aβ,11,11aβ,11bα-dodecahydro-1H-cyclopenta[a]anthracen-3,8-dione, 2β-ethyl-3β-hydroxy-3aβ,6-dimethyl-2,3,3a,4,5,8,9,10,10aβ,11,11aβ,11bα-dodecahydro-1H-cyclopenta[a]anthracen-8-one, 2α-fluoro-3α-hydroxy-3aβ,6-dimethyl-2,3,3a,4,5,8,9,10,10aβ,11,11aβ,11bα-dodecahydro-1H-cyclopenta[a]anthracen-8-one, 2α-fluoro-3β-hydroxy-3aβ,6-dimethyl-2,3,3a,4,5,8,9,10,10aβ,11,11aβ,11bα-dodecahydro-1H-cyclopenta[a]anthracen-8-one, 2α-fluoro-3aβ,6-dimethyl-2,3,3a,4,5,8,9,10,10aβ,11,11aβ,11bα-dodecahydro-1H-cyclopenta[a]anthracen-3,8-dione, 3α-hydroxy-3aβ,6-dimethyl-2,3,3a,4,5,8,9,10,10aβ,11,11aβ,11bα-dodecahydro-1H-cyclopenta[a]anthracen-8-one, 3β-hydroxy-3aβ-methyl-2,3,3a,4,5,8,9,10,10aβ,11,11aβ,11bα-dodecahydro-1H-cyclopenta[a]anthracen8-one, 6-ethyl-3β-hydroxy-3aβ-methyl-2,3,3a,4,5,8,9,10,10aβ,11,11aβ,11bα-dodecahydro-1H-cyclopenta[a]anthracen-8-one, 3aβ-methyl-2,3,3a,4,5,8,9,10,10aβ,11,11aβ,11bα-dodecahydro-1H-cyclopenta[a]anthracene-3,8-dione, 3aβ,6-dimethyl-2,3,3a,8,9,10,10aβ,11,11aβ,11bα-decahydro-1H-cyclopenta[a]anthracene-3,8-dione, 3β-acetoxy-3aβ-methyl-2,3,3a,4,5,8,9,10,10aβ,11,11aβ,11bα-dodecahydro-1H-cyclopenta[a]anthracen-8-one, 3β-acetoxy-3aβ,6-dimethyl-2,3,3a,4,5,8,9,10,10aβ,11,11aβ,11bα-dodecahydro-1H-cyclopenta[a]anthracen-8-one, 3aβ,6-dimethyl-3β-propionyloxy-2,3,3a,4,5,8,9,10,10aβ,11,11aβ,11bα-dodecahydro-1H-cyclopenta[a]anthracen-8-one, 3aβ,6-dimethyl-3β-(4-methoxycarbonylvaleryloxy)-2,3,3a,4,5,8,9,10,10aβ,11,11aβ,11bα-dodecahydro-1H-cyclopenta[a]anthracen-8-one, 3β-ethoxy-3aβ,6-dimethyl-2,3,3a,4,5,8,9,10,10aβ,11,11aβ,11bα-dodecahydro-1H-cyclopenta[a]anthracen-8-one, 3β-(1-cyclohexenyloxy)-3aβ,6-dimethyl-2,3,3a,4,5,8,9,10,10aβ,11,11aβ,11bα-dodecahydro-1H-cyclopenta[a]anthracen-8-one, 3β-[1-(4,4-diethyl)cyclohexenyloxy]-3aβ,6-dimethyl-2,3,3a,4,5,8,9,10,10aβ,11,11aβ,11bα-dodecahydro-1H-cyclopenta[a]anthracen-8-one, 3β-(1-cycloheptenyloxy)-3aβ,6-dimethyl-2,3,3a,4,5,8,9,10,10aβ,11,11aβ,11bα-dodecahydro-1H-cyclopenta[a]anthracen-8-one, 3β-(1-cyclooctenyloxy)-3aβ,6-dimethyl-2,3,3a,4,5,8,9,10,10aβ,11,11aβ,11bα-dodecahydro-1H-cyclopenta[a]anthracen-8-one, 3β-(1-cyclodecenyloxy)-3aβ,6-dimethyl-2,3,3a,4,5,8,9,10,10aβ,11,11aβ,11bα-dodecahydro-1H-cyclopenta[a]anthracen-8-one, 3α-ethynyl-3β-hydroxy-3aβ-methyl-2,3,3a,4,5,8,9,10,10aβ,11,11aβ,11bα-dodecahydro-1H-cyclopenta[a]anthracen-8-one, 2β,3aβ-dimethyl-2,3,3a,4,5,8,9,10,10aβ,11,11aβ,11bα-dodecahydro-1H-cyclopenta[a]anthracene-3,8-dione, 2α-chloro-3aβ,6-dimethyl-2,3,3a,4,5,8,9,10,10aβ,11,11aβ,11bα-dodecahydro-1H-cyclopenta[a]anthracen-3,8-dione, 3β-hydroxy-2β,3aβ-dimethyl-2,3,3a,4,5,8,9,10,10aβ,11,11aβ,11bα-dodecahydro-1H-cyclopenta[a]anthracen-8-one, 2α-fluoro-3β-hydroxy-3aβ,6-dimethyl-2,3,3a,4,5,8,9,10,10aβ,11,11aβ,11bα-dodecahydro-1H-cyclopenta[a]anthracen-8-one, 2α-bromo-3β-hydroxy-3aβ,6-dimethyl-2,3,3a,4,5,8,9,10,10aβ,11,11aβ,11bα-dodecahydro-1H-cyclopenta[a]anthracen-8-one, 2β-bromo-3β-hydroxy-3aβ,6-dimethyl-2,3,3a,4,5,8,9,10,10aβ,11,11aβ,11bα-dodecahydro-1H-cyclopenta[a]anthracen-8-one, 2α,3β-dihydroxy-3aβ,6-dimethyl-2,3,3a,4,5,8,9,10,10aβ,11,11aβ,11bα-dodecahydro-1H-cyclopenta[a]anthracen-8-one, 3α-hydroxy-3aβ,6-dimethyl-2,3,3a,4,5,8,9,10,10aβ,11,11aβ,11bα-dodecahydro-1H-cyclopenta[a]anthracen-8-dione, 2α-chloro-3α-hydroxy-3aβ,6-dimethyl-2,3,3a,4,5,8,9,10,10aβ,11,11aβ,11bα-dodecahydro-1H-cyclopenta[a]anthracen-8-one, and 2α-bromo-3α-hydroxy-3aβ,6-dimethyl-2,3,3a,4,5,8,9,10,10aβ,11,11aβ,11bα-dodecahydro-1H-cyclopenta[a]anthracen-8-one, or the ketal derivatives thereof.

The numbering of cyclopenta[a]anthracene in the fundamental structure of the compounds of the present invention is as follows.

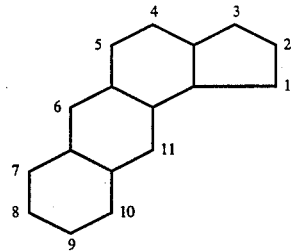

⑤ 6-ethyl-3β-hydroxy-3aβ-methyl-1,2,3,3a,4,5,8,9-,9aβ,9bα-decahydro-7H-benzo[e]inden-7-one [France Pat. No. 1359675, (1963)]

In the reaction scheme, R, R', R'', the dotted line and the wavy line each has the same meanings as defined above. $X^1$ is hydroxymethyl or halomethyl; $X^2$ is lower alkyl, halogen atom, or hydroxy; and Z is ketal protecting group. When the 5a,6-double bond does not exist, the configuration at the 6 position is α.

Reaction Scheme

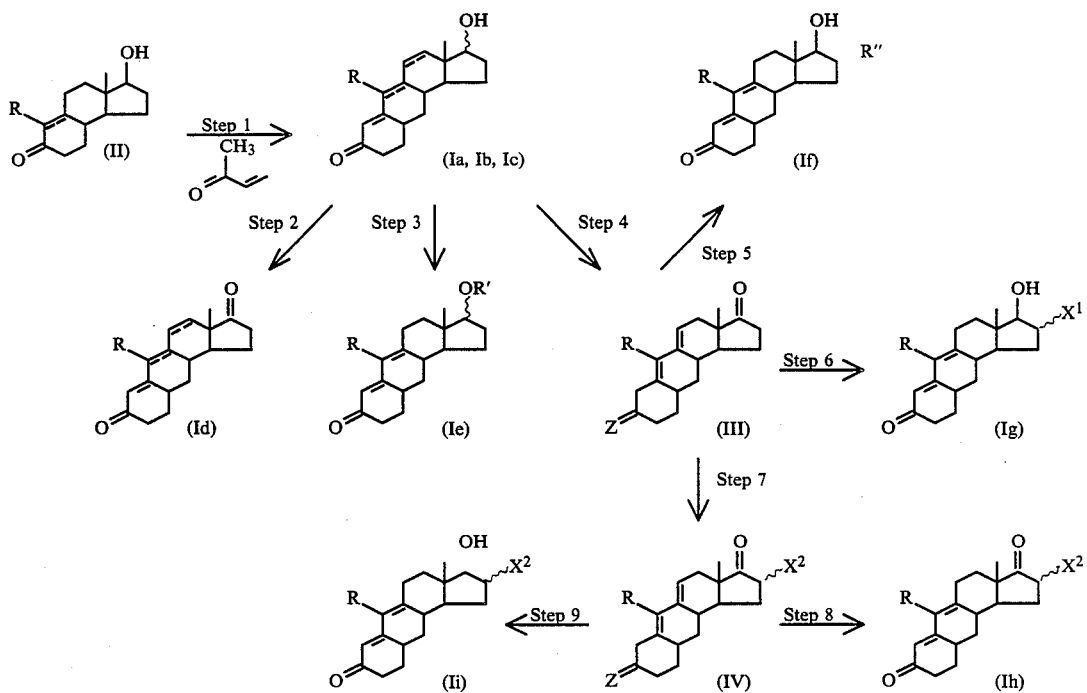

Each step is described in detail below.

The ketal derivative of the substituted anthrasteroid derivative represented by the above mentioned general formula (I) refers to the dialkylketal of 8-carbonyl, e.g., dimethylketal, diethylketal or alkyleneketal, e.g., ethyleneketal, trimethyleneketal. In this case, the double bond at the 6a,7 position moves to 6,6a and the 5a,6-double bond, if it exists, moves to 5,5a.

The aimed compound (I) of the present invention can be prepared from the known perhydrocyclopentenonaphthalene derivatives of the formula (II) according to the following reaction scheme.

In this reaction the following compounds are exemplified as starting material (II).

① 3β-hydroxy-3aβ-methyl-1,2,3,3a,4,5,5aα,6,8,9,9aβ,-9bα-dodecahydro-7H-benzo[e]inden-7-one [(H. M. Alanis et al., J.Med.Chem., 28, 1796, (1985)]

② 3β-hydroxy-3aβ,6α-dimethyl-1,2,3,3a,4,5,5aα,6,8,9-,9aβ,9bα-dodecahydro-7H-benzo[e]inden-7-one [(M. P. Hartshorn et al., J.Chem.Soc., 1312, (1962)]

③ 3β-hydroxy-3aβ-methyl-1,2,3,3a,4,5,8,9,9aβ,9bα-decahydro-7H-benzo[e]inden-7-one [France Pat. No. 1476509, (1963)]

④ 3β-hydroxy-3aβ,6-dimethyl-1,2,3,3a,4,5,8,9,9aβ,-9bα-decahydro-7H-benzo[e]inden-7-one [M. P. Hartshorn et al., J.Chem.Soc., 1312, (1962)]

Step 1

In this step, methyl vinyl ketone or its equivalent (e.g., 1-diethylamino-3-butanone, 1,3-dichloro-2-butene) is condensed with the starting material (II) in the presence of a base (Michael condensation) to form the ring A which corresponds to the ring A of steroid. If necessary, the double bond may be introduced between the 4 and 5 positions of the ring C.

The condensation forming the ring A is carried out according to the method utilized for total synthesis of steroids. For example, in case where no 5a, 6-double bond exists in the starting material (II), the compound (Ia) (which does not have 4, 5 and 5a, 6-double bonds) in the reaction scheme is prepared as follows. The compound (II) is allowed to react with a formate (e.g., ethyl formate) to introduce hydroxymethylene at 8 position, then 3-oxobutyl is introduced to the activated 8 position by the reaction with methyl vinyl ketone, and then the resulting compound is cyclized to give the compound (Ia).

The reaction of the compound (II) with the formate ester is carried out in the presence of a strong base such as lithium hydride, sodium hydride, sodium amide in an ether such as diethyl ether, tetrahydrofuran, dimethoxyethane under a dry condition with cooling or at about room temperature. The reaction of the prepared 8-hydroxymethylene compound with methyl vinyl ketone is carried out according to the condition of Michael condensation, for example, in the presence of a base (organic base such as triethylamine, N,N-dimethylaniline, collidine, or the like is preferably used) in an above mentioned ether solvent at about room temperature, if necessary, under cooling or heating. The product, 8-formyl-8-(3-oxobutyl) compound is easily cyclized to the aimed compound (Ia) by treating with an acid or alkali.

When the starting material (II) has a 5a, 6-double bond, methyl vinyl ketone may be allowed to react directly with the compound (II). However, it is preferable that before allowed to react with methyl vinyl ketone, the 7-carbonyl is treated with metal amide (e.g., lithium diisopropylamide, lithium bis(trimethylsilylamide)) to give an enolate, which is then allowed to react methyl vinyl ketone after silylation or directly with 1,3-dichloro-2-butene. The reaction is carried out in a conventional reaction condition as described in the example. In this reaction, the compound (Ib) (having 5a, 6-double bond) is prepared.

In addition, in this step, the 3-hydroxy may be protected with a proper protecting group such as acyl (e.g., acetyl, propionyl, benzoyl) or ether-type protecting group (e.g., tetrahydropyranyl, methoxymethyl), if necessary. The protecting group may be selected corresponding to the reaction condition of this step.

The introduction of 4, 5 double bond into the ring C is carried out as follows; the 8-carbonyl is enolated to move the 5a, 6 double bond to 5, 5a, then the 5 position is halogenated with a halogenating agent such as N-bromosuccinimide or N-chlorosuccinimide and then the resulting halide is dehydrohalogenated. All these reactions are carried out according to a conventional methods. In this reaction, the compound (Ic) (having 4, 5 and 5a, 6 double bonds) is prepared.

The β-hydroxy at 3 position is converted into α-hydroxy by reaction with triphenylphosphine, benzoic acid and azodicarboxylate and subsequent hydrolysis of the resulting 3α-benzoate.

Step 2

In this step, the 3-hydroxy of the compound (Ia to c) is oxidized to give the 3-oxo compound (Id). The oxidation in this step is carried out according to the conventional method for oxidizing a hydroxy to carbonyl. In this reaction, the oxidation with an oxidizing agent such as ruthenium tetroxide, chromic acid, or the like or Oppenauer oxidation is preferably applicable. Especially, the oxidation with chromic acid, for example, chromic acid/pyridine, chromic acid/aqueous acetic acid, chromic acid/acetone/sulfuric acid (Jones' reagent) or the like is preferable.

Step 3

In this step, various substituents corresponding to R' of the general formula (I) are introduced to the 3-hydroxy of the compound (Ia to b) to give the ether derivatives or ester derivatives (Ie).

The substituent corresponding to R' is the same as mentioned above. The ether derivatives in the compound (Ie) are prepared as follows. The 8-carbonyl of the compound (Ia to b) is protected, then an alkyl halide corresponding to the desired lower alkyl is allowed to react with the resulting compound in the presence of a strong base, and the 8-protecting group is removed to regenerate the carbonyl or the compound (Ia to b) is directly allowed to react with a 1-lower alkoxycycloalkene. Depending on the reaction condition, the alkoxy cycloalkyl which is prepared by the reaction with the 1-lower alkoxycycloalkene is converted into cycloalkenyl by eliminating the alkoxy.

The reaction of the compound (Ia to b) with the alkyl halide is carried out under ordinary alkylation condition of hydroxy, for example, in the presence of a base such as sodium hydride, sodium amide, potassium t-butoxide in an aprotic solvent such as diethyl ether, tetrahydrofuran, benzene, toluene, or the like under cooling or heating. Example of the alkyl halide is methyl iodide, ethyl bromide, propyl bromide, isopropyl bromide, butyl iodide, isobutyl bromide, pentyl chloride, s-pentyl bromide, or the like.

Before the etherification in this step, the 8-carbonyl may be protected with an enol-ether or ketal protecting group (e.g., methyl enol ether, ethyl enol ether, ethylene ketal, or the like). The enolation or ketalation is carried out in a conventional manner, in the presence of an acidic catalyst such as p-toluenesulfonic acid by reaction with trimethyl orthformate, triethyl orthoformate, ethlene glycol, or the like. By introducing the enol-ether or ketal protecting group, the 6a, 7-double bond moves to 6, 6a position. After etherification, the elimination of enol-ether or ketal protecting group is easily achieved by treatment in an acidic aqueous solution such as dilute hydrochloric acid or dilute sulfuric acid or its solution in alcohol or acetone at room temperature.

The reaction of the compound (Ia to b) with a 1-lower alkoxycycloalkene is carried out in the presence of an acidic catalyst under cooling or at room temperature. As an acidic catalyst, hydrochloric acid or p-toluenesulfonic acid or their pyridinium salt, phosphorus oxychloride, or the like is exemplified. The solvent such as benzene, toluene, hexane, dichloromethane, chloroform, or the like is used, if necessary. Examples of the 1-lower alkoxycycloalkene include 1-methoxycyclopentene, 1-ethoxycyclopentene, 1-ethoxycyclohexene and 1-methoxycycloheptene.

The ester derivative represented by the general formula (Ie) has an ester linkage between the 3-hydroxy and the aliphatic lower acyl which may have carboxy or its lower alkyl ester in the other end and examples of such ester derivatives are the same as mentioned above. The said ester derivative can be prepared by reacting the compound (Ia to b) with an anhydride, halide or activated ester of the aliphatic acyl according to the conventional manner.

Step 4

In this step, the 8-carboxy of the compound (Ib) is protected with ketal and then the 3-hydroxy is oxidized to the compound (III).

The ketal-formation at the 8-carbonyl is carried out in the same manner as described in Step 3. The oxidation of 3-hydroxy is carried out by the method using an oxidizing agent, for example, chromic acid/pyridine, chromic acid-pyridine complex/dichloromethane, pyridinium chlorochromate/dichloromethane.

Step 5

In this step, a lower alkyl or lower alkynyl is introduced to the 3-carbonyl of the compound (III) to give the compound (If).

The reaction in this step is carried out according to the ordinary method of introducing an alkyl or alkynyl to the 17-carbonyl of steroid. The reaction is carried out according to a method for the addition of alkyl or alkynyl to carbonyl, for example, with an alkali metal salt of alkyl or alkynyl (e.g., methyl lithium, sodium acetylide, potassium acetylide) or with the correspondence Grignard reagent (e.g, methylmagnesium chloride, ethylmagnesium bromide, ethynylmagnesium bromide). The reaction is usually carried out in a dry ether solvent such as diethyl ether, tetrahydrofuran, or diethoxyethane under cooling or at room temperature, or if necessary, under heating. In the case where an alkali metal acetylide is use, the reaction may be carried out in liquid ammonia.

After the alkylation or alkynylation, the 8-protecting group may be removed by conventional acid treatment to give the aimed compound (If).

Step 6

In this step, a hydroxymethine is introduced to the 2-active methylene of the compound (III) and then the resulting compound is reduced and deprotected to give the compound (Ig) ($X_1$=hydroxymethyl), which may be further halogenated to give the compound (Ig) ($X_1$=halomethyl).

The introduction of 2-hydroxymethine to the compound (III) is achieved by the reaction with a formate such as methyl formate, ethyl formate, or the like. The reaction is carried out in the presence of a strong base such as lithium hydride, sodium hydride, lithium amide, lithium diisopropylamide, in an aprotic solvent such as benzene, toluene, diethyl ether, tetrahydrofuran, dimethylsulfoxide, or dimethylformamide or their mixture at a low temperature or room temperature. The intermediate represented by the following general formula (V) is prepared through the above reaction.

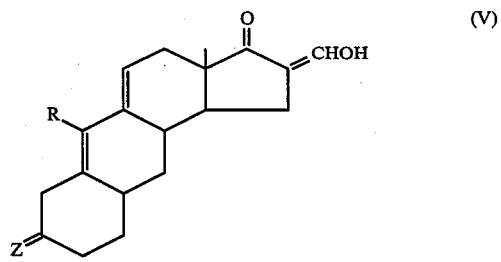

(wherein R and Z each is the same as defined above.)
The reductions of the 3-carbonyl and the double bond of 2-methine in the compound (V) are carried out by hydride reduction with a reducing agent such as sodium or potassium borohydride or sodium cyanoborohydride or the like. The reaction is carried out in a solvent such as methanol, ethanol, tetrahydrofuran, dioxane, or dimethoxyethane or their mixture at or around room temperature. The aimed compound (Ig) ($X^1$=hydroxymethyl) is prepared by treating the product with an acid in a conventional manner to remove the ketal protecting group. The 3-hydroxy of the compound (Ig) have $\beta$-configuration, while 2-hydroxymethyl is a mixture of $\alpha$ and $\beta$-configuration. This mixture can easily be separated by chromatography.

The halogenation of the compound (Ig) ($X^1$=hydroxymethyl) may be carried out by direct halogenation with an ordinary halogenating agent such as thionyl chloride, thionyl bromide, phosphorus trichloride, phosphorus tribromide, phosphorus pentachloride, or oxalyl chloride. Preferably, the hydroxy is once converted into p-toluenesulfonyloxy or methanesulfonyloxy and then halogenated with an alkali metal halide such as lithium bromide, sodium bromide, lithium bromide. The p-toluenesulfonyloxy or methanesulfonyloxy derivative is prepared by reacting hydroxymethyl derivatives with p-toluenesulfonyl chloride or methanesulfonyl chloride in the presence of a base in a proper solvent. The resulting p-toluenesulfonyloxy or methanesulfonyloxy derivative is allowed to react with an alkali metal halide in a proper solvent at room temperature or under reflux with heating.

Step 7

In this step, lower alkyl, halogen, or hydroxy is introduced to the 2-active methylene of the intermediate (III) to give the intermediate (IV).

7-a: Introduction of a lower alkyl

The reaction is carried out according to the ordinarily condition of the alkylation of active methylene with an alkyl halide in the presence of a strong base. As a strong base, alkali metal alkoxide, e.g., potassium t-butoxide, hydride, e.g., lithium hydride, sodium hydride, or alkali metal amide, e.g., lithium amide, sodium amide, potassium amide, lithium diisopropylamide, is exemplified. As an alkyl halide which corresponds to the alkyl to be introduced, for example, methyl bromide, ethyl iodide, propyl chloride, isopropyl bromide, butyl iodide, or the like is exemplified. The reaction is carried out in a solvent selected among t-butanol, diethyl ether, tetrahydrofuran, diethoxyethane, dimethylformamide, dimethylsulfoxide, or hexamethylphosphoric triamide dependently on the property of the base used, in a dry condition under cooling or at room temperature. The alkyl introduced in this step is usually obtained as a mixture of $\alpha$ and $\beta$ configuration. By isomerization with an alkali (e.g., sodium hydroxide, potassium hydroxide) in ethanol, the mixture can be converted to the isomer of $\beta$ configuration.

7-b: Introduction of halogen

The halogenation in this step is carried out in a neutral or basic condition in order to avoid influence on the 8-ketal protecting group. Preferably, the reaction is carried out in approximately the same condition as that of the above mentioned step 7-a, that is, the reaction with bromine ($Br_2$), N-bromosuccinimide or N-chloroacetamide in the presence of a strong base at a low temperature.

As an alternative method, before the reaction with the halogenating agent, the 3-carbonyl is converted to an enol (e.g., ethyl enol ether, enol acetate, silyl enol ether) or an enamine (e.g., piperidine enamine, morpholine enamine) in order to activate the 2-methylene. For example, the 3-carbonyl is enolated with trimethylsilyl and then, 2-methylene is fluorinated with xenon difluoride or N-fluoropyridinium triflate to give a 2$\alpha$-fluoro-compound. As fluorinating agent, perchloryl fluoride is also often used. In particular, in the case where halogen is fluorine, the 2-hydroxy compound described in the following step 7-c may be fluorinated as shown in Example (21).

7-c: Introduction of hydroxy

The halogen derivative (IV) ($X^2$=halogen) prepared in the above mentioned (step 7-b), especially, the bromine of the bromo derivative is substituted by a hydroxy to give (IV) (X²=hydroxy). In this step, the reaction is carried out in the presence of an alkali metal hydroxide such as sodium hydroxide or potassium hydroxide in a proper solvent such as dimethylformamide or dimethylsulfoxide at a low temperature or room temperature.

Step 8

In this step, the 8-ketal protecting group of the intermediate (IV) prepared in the previous step is removed by acid treatment in the conventional manner to give the aimed compound (Ih) (X²=lower alkyl, halogen, or hydroxy). The reaction is carried out according to the method described in Step 3.

Step 9

In this step, the 3-carbonyl of the intermediate (IV) prepared in Step 7 is reduced and then the ketal is removed to give the 3-hydroxy compound (Ii) (X has the same meaning as mentioned above). The reduction and deprotection in this step, may be carried out according to the manner as described in Step 6. In the reduction in this step, the resulting hydroxy may be of a mixture of α and β configuration which is influenced by the substituent at 2-position.

Effect of the Invention

The aimed compounds of the present invention which have a potent anti-androgenic action with lower side effect are useful for the treatment of androgen-dependent diseases such as prostatic hypertrophy, prostatic cancer, or the like.

The aimed compound of the present invention can be administered orally or paranterally. For oral administration, the aimed compound of the present invention can be used as conventional preparations, for example, solid preparation such as tablet, powder, capsule, or granule, or liquid preparation such as aqueous or oily suspension, syrup, or elixir. For parenteral administration, the aimed compound of the present invention can be used as aqueous or oily suspension for injection. On its preparation, all of the ordinarily used vehicle, binder, lubricant, aqueous solvent, oily solvent, emulsifier, suspending agent, or the like can be used and other additives such as preservative, stabilizer, or the like may be contained therein.

The aimed compound of the present invention is generally administered in amounts of 50 mg to 500 mg once or twice a week by oral administration and 5 mg to 50 mg once or twice a week by subcutaneous injection; the dosage may be determined depending on administration route, patient's age, weight, and condition, and kind of disease.

The following examples are included to explain the embodiment of the present invention in more detail, but these are not intended to limit the scope of the invention. Every compound shown in the examples is an optically active one. For example, the absolute configuration of the compound (4) at 3 position shown in Example 1 is (3S) and it has the same absolute configuration as the compound in other examples.

EXAMPLE 1

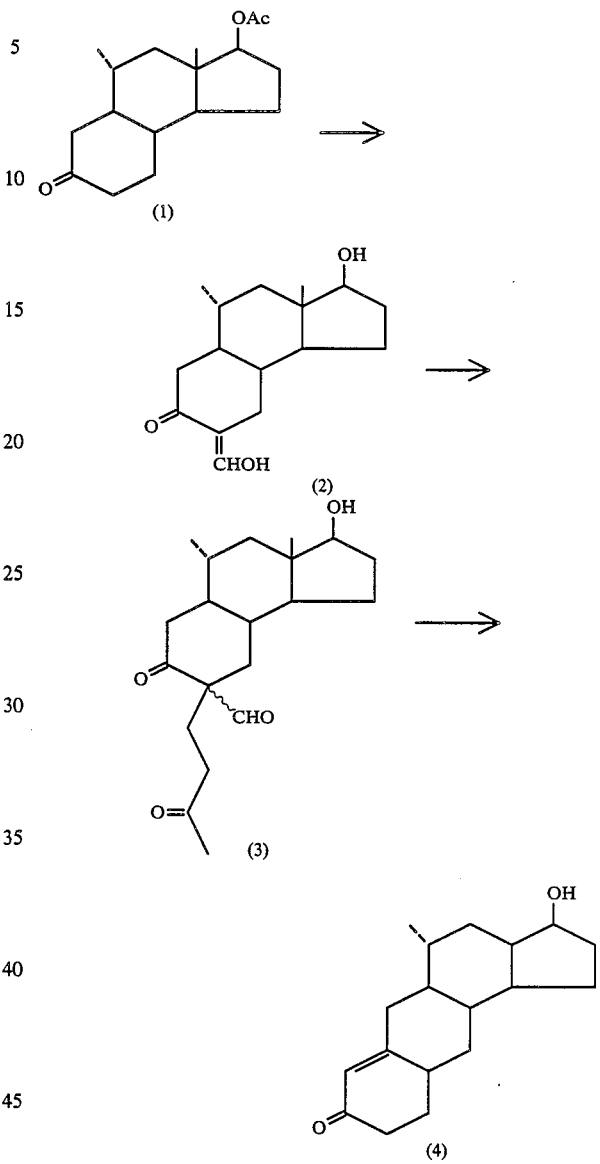

(1) 3β-acetoxy-3aβ,6α-dimethyl-1,2,3,3a,4,5,5aα,6,8,9-,9aβ,9bα-dodecahydro-7H-benzo[e]inden-7-one
(2) 3β-hydroxy-8-hydroxymethylene-3aβ,6α-dimethyl-1,2,3,3a,4,5,5aα,6,8,9,9aβ,9bα-dodecahydro-7H-benzo[e]inden-7-one
(3) 8-formyl-3β-hydroxy-3aβ,6α-dimethyl-8-(3-oxobutyl)-1,2,3,3a,4,5,5aα,6,8,9,9aβ,9bα-dodecahydro-7H-benzo[e]inden-7-one
(4) 3β-hydroxy-3aβ,6α-dimethyl-2,3,3a,4,5,-,5aα,6,8,9,10,10aβ,11,11aβ,11bα-tetradecahydro-1H-cyclopenta[a]anthracen-8-one (i) To a solution of 7.5 g of the compound (1) in 150 ml of dry ether is added 8 ml of ethyl formate and then 3 g of sodium hydride (oil, 50%) with ice cooling under stirring and the mixture is stirred at the same temperature for an hour. After allowed to stand at room temperature overnight, the reaction mixture is poured into chilled water and separated. The aqueous layer is acidified with 2N hydrochloric acid and extracted with ether. The extract is washed with water, dried over sodium sulfate, and concentrated under reduced pressure to give 6.5 g of the compound (2) as an oil in 91% yield.

NMRδ ppm(CDCl₃): 0.79 (3H,s), 1.23 (3H,d,J=7 Hz), 3.71 (1H,t,J=8 Hz), 8.60 (1H,s).

IRν max(film) cm⁻¹: 3400, 1727, 1707, 1634, 1582.

(ii) To a solution of 6.4 g of the compound (2) in 10 ml of methyl vinyl ketone is added 6.1 ml of triethylamine under ice cooling and the mixture is allowed to stand at room temperature for 3 days. The reaction mixture is concentrated and the residue dissolved in ether is successively washed with 0.2N hydrochloric acid, water, 5% aqueous solution of sodium hydrogencarbonate, and water, dried over sodium sulfate, and concentrated to give 5.7 g of the compound (3) as an oil in 70% yield.

NMRδ ppm(CDCl₃): 0.83 (3H,s), 1.00 (3H,d,J=7 Hz), 2.10 (3H,s), 3.68 (1H,t,J=8 Hz), 9.60 (1H,s).

IRν max(film)cm⁻¹: 3425, 2725, 1716, 1693.

(iii) To a solution of 5.65 g of the compound (3) prepared above in 80 ml of ethanol is added 20 ml of 10% aqueous solution of potassium carbonate in a nitrogen atmosphere and the mixture is refluxed for 5 hours. After cooling, the reaction mixture is concentrated. The residue dissolved in ether is washed with water, dried over sodium sulfate, and concentrated under reduced pressure. The residue is chromatographed [silica gel, Merck, Lobar C, eluted with benzene-ethyl acetate (2:1)] to give 4.29 g of the compound (4) in 87% yield. Colorless prisms.

Mp. 122° C. to 124° C.

NMRδ ppm(CDCl₃): 0.80(3H,s), 1.08(3H,d,J=7 Hz), 3.67(1H,t,J=8 Hz), 5.88(1H,s).

IRν max(Nujol)cm⁻¹: 3305, 3260, 1668, 1618.

UVλ max(EtOH)nm: 243 (ε=15600).

[α]_D +47.3±1.8° (c=0.495, CHCl₃).

Anal. Calcd. (%) for C₁₉H₂₈O₂:
C 79.12, H 9.79, Found (%): C 79.00, H 9.54.

EXAMPLE 2

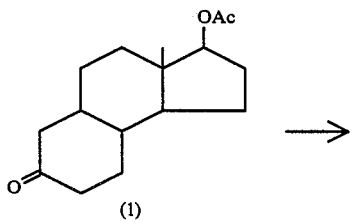

(1) 3β-acetoxy-3aβ-methyl-1,2,3,3a,4,5,5aα,6,8,9,9aβ,-9bα-dodecahydro-7H-benzo[e]inden-7-one (2) 3β-hydroxy-3aβ-methyl-2,3,3a,4,5,5aα,6,8,9,10,-10aβ,11,11aβ,11bα-dodecahydro-1H-cyclopenta[a]anthracen-8-one

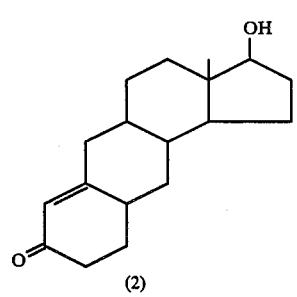

The compound (2) is prepared from the compound (1) in the same manner as in Example 1.

Colorless prisms, Mp. 158° C. to 160° C.

NMRδ ppm(CDCl₃): 0.80(3H,s), 3.65(1H,t,J=8 Hz), 5.78(1H,s).

IRν max(Nujol)cm⁻¹: 3564, 1667, 1626.

UVλ max(EtOH)nm: 241 (ε=17200).

[α]_D −29.2±0.8° (C=0.514, CHCl₃)

Anal. Calcd. (%) for C₁₈H₂₆O₂:
C 78.79, H 9.55, Found(%): C 78.77, H 9.81

EXAMPLE 3

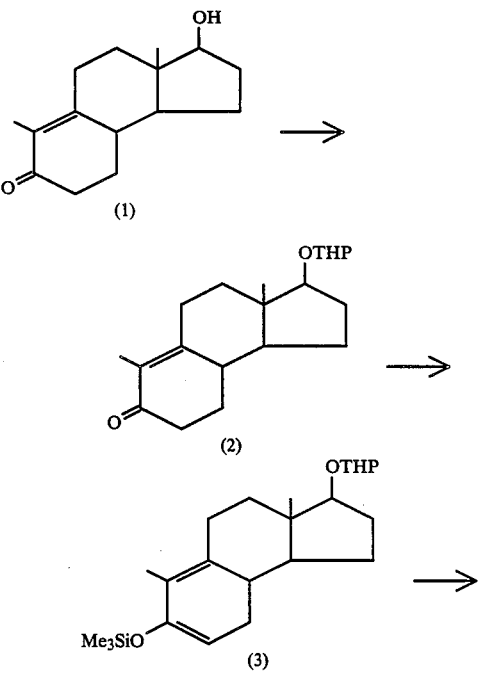

(1) 3β-hydroxy-3aβ,6-dimethyl-1,2,3,3a,4,5,8,9,9aβ,-9bα-decahydro-7H-benzo[e]inden-7-one (2) 3β-(2-tetrahydropyranyloxy)-3aβ,6-dimethyl-1,2,3,3a,4,5,8,9,9aβ,9bα-decahydro-7H-benzo[e]inden-7-one (3) 3aβ,6-dimethyl-3β-(2-tetrahydropyranyloxy)-7-trimethylsilyloxy-1,2,3,3a,4,5,9aβ,9bα-octahydro-9H-benzo[e]indene (4) 3β-hydroxy-3aβ,6-dimethyl-2,3,3a,4,5,8,9,10,-10aβ,11,11aβ,11bα-dodecahydro-1H-cyclopenta[a]anthracen-8-one (i) To a solution of 20 g of the compound (1) in 200 ml of dichloromethane are added 10 ml of dihydropyran and 2.5 g of pyridinium p-toluenesulfonate and the mixture is stirred for 6 hours. The dichloromethane is evaporated under reduced pressure at room temperature. The residue dissolved in 500 ml of ether is washed with a saturated aqueous solution of sodium chloride three times, dried over sodium sulfate, and concentrated under reduced pressure to give 27.2 g of the crude compound (2) in 100% yield. Pale yellow oil.

NMRδ ppm(CDCl₃): 0.92(3H,s), 1.78(3H,s), 3.35~4.06(3H,m), 4.62(1H,brs).

IRν max(film)cm⁻¹: 1662, 1603.

(ii) To a solution of lithium diisopropylamide, which is prepared from 20.5 ml of diisopropylamine and 91 ml of 1.6N n-butyllithium in hexane, in 200 ml of tetrahydrofuran is added a solution of 27.1 g of the compound (2) prepared above in 100 ml of dry tetrahydrofuran at −20° C. over 30 minutes in nitrogen atmosphere under stirring. The mixture is stirred at the same temperature for an hour and then a solution of 18.6 g of chlorotrimethylsilane in 100 ml of dry tetrahydrofuran is added dropwise over 10 minutes. After the mixture is stirred at the same temperature for an hour, 20 ml of water is added in small portions to decompose lithium diisopropylamide. Tetrahydrofuran is evaporated under reduced pressure at room temperature and the residue dissolved in 600 ml of ether is washed with a saturated aqueous solution of sodium chloride three times, dried over sodium sulfate and evaporated under reduced pressure to give 33.3 g of the crude product (3) in 100% yield. Pale yellow oil.

NMRδ ppm(CDCl₃): 0.36(9H,s), 0.78(3H,s), 1.67(3H,s), 3.33~4.07(3H,m), 4.64(1H,brs), 4.87 (1H,dd,J=6 and 2 Hz).

(iii) To a solution of 33.2 g of the compound (3) prepared above in 400 ml of dichloromethane is added 7 g of methyl vinyl ketone and the mixture is cooled at −78° C. in a nitrogen atmosphere. To the mixture is added 80 ml of dichloromethane containing 12.15 g of titanium tetraisopropoxide and 9.4 ml of titanium tetrachloride over 30 minutes under stirring and the resulting mixture is stirred for 3 hours at the same temperature. The reaction mixture to which is added 150 ml of 10% aqueous solution of potassium carbonate in small portions to decompose is extracted with dichloromethane. The dichloromethane layer is washed with water, dried, and concentrated under reduced pressure to give 39 g of oil.

Then, to the solution of the oil in 360 ml of ethanol is added 20 ml of 2N hydrochloric acid and the mixture is allowed to stand overnight. After the mixture is neutralized with 2N sodium carbonate, ethanol is evaporated under reduced pressure. The residue added water is extracted with dichloromethane. The dichloromethane layer is washed with water, dried, and concentrated under reduced pressure to give 30.6 g of oil.

To a solution of resulting oil in 260 ml of methanol is added 40 ml of 20% aqueous solution of potassium hydroxide in a nitrogen atmosphere and the mixture is refluxed for 2 hours. After cooling, the reaction mixture is neutralized with 4N hydrochloric acid and methanol is evaporated under reduced pressure. The residue added water is extracted with dichloromethane three times, washed with water, dried over sodium sulfate, and concentrated under reduced pressure. The residue is chromatographed [120 g of silica gel and Lobar column (Merck), benzene-ethyl acetate (3:1)] to give 15.7 g of crude crystals, which is recrystallized from a mixture of dichloromethane-ether to give 14.6 g of the compound (4) in 60% yield as colorless prisms. Mp. 149° C. to 150° C.

Anal. Calcd. (%) for C₁₉H₂₆O₂: C 79.68, H 9.15, Found (%): C 79.48, H 9.25.

The compound (3-5), (3-6) shown in Table 1 can be prepared in the same manner.

EXAMPLE 4

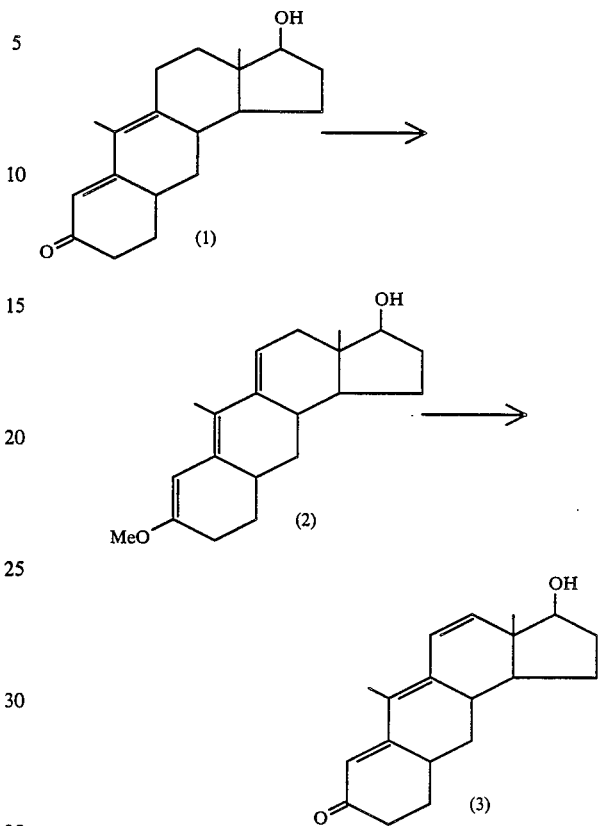

(1) Same as the compound (4) in Example 3
(2) 3β-hydroxy-8-methoxy-3aβ,6-dimethyl-2,3,3a,4,9,10,10aβ,11,11aβ,11bα-decahydro-1H-cyclopenta[a]anthracene
(3) 3β-hydroxy-3aβ,6-dimethyl-2,3,3a,8,9,10,10aβ,11,-11aβ,11bα-decahydro-1H-cyclopenta[a]anthra cen-8-one (i) To a solution of 4.0 g of the compound (1) in 70 ml of methanol are added 4.0 ml of methyl orthoformate and 30 mg of p-toluenesulfonic acid and the mixture is stirred at room temperature for 30 minutes. The reaction mixture is poured into 50 ml of 5% aqueous solution of sodium hydrogencarbonate and extracted with ether. The ether layer is washed with water, dried and concentrated under reduced pressure to give the crude crystals, which is recrystallized from methanol to give 3.00 g of the compound (2) in 72% yield as colorless needle crystals. Mp. 120° C. to 124° C.

NMRδ ppm(CDCl₃): 0.74(3H,s), 1.82(3H,s), 3.62(3H,s), 3.77(1H,m), 5.58(1H,brs), 5.62(1H,s).

(ii) To a solution of 2.62 g of compound (2) prepared above in 180 ml of acetone are added 18 ml of 10% sodium acetate and 1.94 g of N-bromosuccinimide under stirring and then 1.8 ml of acetic acid is added thereto, and the resulting mixture is stirred at room temperature for an hour. The reaction mixture is concentrated under reduced pressure and the residue dissolved in ethyl acetate is successively washed with water, 5% aqueous solution of sodium thiosulfate, water, 0.2N sodium carbonate, water, a saturated aqueous solution of sodium chloride, and water, dried, and concentrated under reduced pressure to give 2.81 g of pale yellow powder.

Then, to a solution of this powder in 20 ml of dry dimethylformamide are added 2.0 g of lithium bromide (anhydride) and 2.0 g of lithium carbonate and the mixture is stirred at 150° C. for 5 hours in a nitrogen atmosphere. After cooling, the reaction mixture is poured into chilled water and extracted with ethyl acetate twice. The ethyl acetate layer is washed with water and a saturated aqueous solution of sodium chloride, dried over sodium sulfate, and concentrated under reduced pressure. The residue is chromatographed [silica gel, Merck, Lobar C, eluted with benzene-ethyl acetate (2:1)] to give 1.00 g of the compound (3) in 40% yield as colorless prisms.

Mp. 221° C. to 223° C.

NMRδ ppm(CDCl$_3$): 0.91(3H,s), 1.90(3H,d,J=2 Hz), 3.89(1H,m), 6.08 (1H,s), 6.42(1H,d,J=10 Hz), 6.51 (1H,d,J=10 Hz).

IRν max(Nujol)cm$^{-1}$: 3370, 1627, 1558, 1325, 1273, 1200.

UVλ max(EtOH)nm: 338 (ε=36700).

[α]$_D$ −357.5±7.9° (c=0.505, CHCl$_3$).

Anal. Calcd. (%) for C$_{19}$H$_{24}$O$_2$: C 80.24, H 8.51, Found(%): C 79.99, H 8.47

EXAMPLE 5

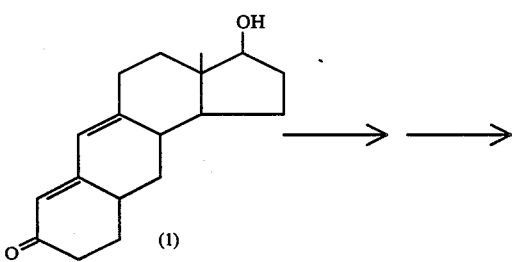

(1)  3β-hydroxy-3aβ-methyl-2,3,3a,4,5,8,9,10,10aβ,11,-11aβ,11bα-dodecahydro-1H-cyclopenta[a]anthracen-8-one
(2)  3β-hydroxy-3aβ-methyl-2,3,3a,8,9,10,10aβ,11,-11aβ,11bα-decahydro-1H-cyclopenta[a]anthracen-8one The corresponding compound (2) is prepared from the compound (1) in the same manner as in Example 4.

Colorless prisms. Mp. 154.5° C. to 155.5° C. NMRδ ppm(CDCl$_3$):  0.91(3H,s),  3.90(1H,brt,J=8  Hz), 5.79(1H,s), 6.03(1H,d,J=9 Hz), 6.05(1H,d,J=9 Hz).

IRν max(Nujol)cm$^{-1}$: 3390, 1641, 1635, 1325, 1269, 1258, 1195, 1080.

UVλ max(EtOH)nm:333.5(ε=19900)

[α]$_D$ −398.6±14.1° (c=0.298, CHCl$_3$)

Anal. Calc. (%) for C$_{18}$H$_{22}$O$_2$: C 79.96, H 8.20, Found (%): C 80.16, H 8.14.

EXAMPLE 6

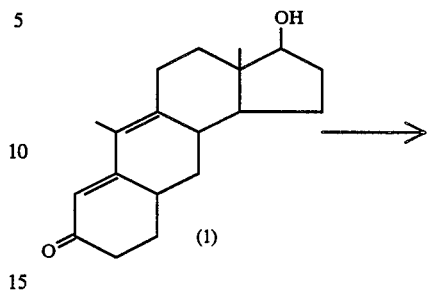

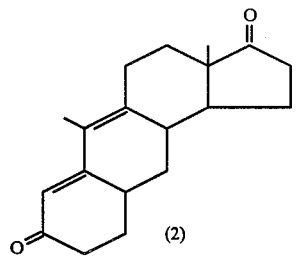

(1) Same as the compound (4) in Example 3

(2) 3aβ,6-dimethyl-2,3,3a,4,5,8,9,10,10aβ,11,11aβ,11bα-dodecahydro-1H-cyclopenta[a]anthracene-3,8-dione To a solution of 1.19 g of the compound (1) in 50 ml of acetone is added 1.6 ml of Jone's reagent at 0° C. and the mixture is stirred at the same temperature for 20 minutes. The reaction mixture to which is added 30 ml of chilled water and concentrated under reduced pressure. The residue dissolved in ethyl acetate is successively washed with water, 5% solution of sodium hydrogencarbonate, water, and a saturated aqueous solution of sodium chloride, dried over sodium sulfate, and concentrated. The residue is crystallized from a mixture of ethyl acetate and ether to give 1.07 g of the compound (2) in 91% yield as colorless prisms. Mp. 178° C. to 181° C.

Anal. Calcd. (%) for C$_{19}$H$_{24}$O$_2$: C 80.24, H 8.51, Found (%): C 79.97, H 8.42.

The compounds (6-3) and (6-4) shown in Table 2 can be prepared in the same manner.

EXAMPLE 7

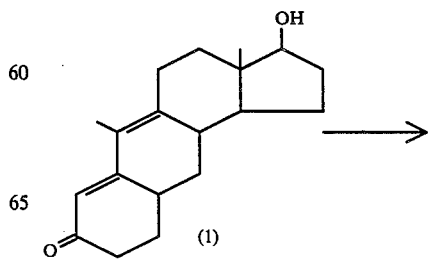

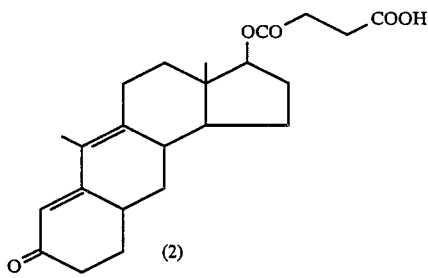

(1) Same as the compound (4) in Example 3.
(2) 3aβ,6-dimethyl-3β-(3-carboxypropionyloxy)-2,3,3a,4,5,8,9,10,10aβ,11,11aβ,11bα-dodecahydro-1H-cyclopenta[a]anthracen-8-one.

To a solution of 143 mg of the compound (1) in 2 ml of pyridine are added 200 mg of succinic acid anhydride and 120 mg of dimethylaminopyridine, and the mixture is stirred for 1 hour. After allowed to stand overnight, the reaction mixture is poured into 50 ml of chilled water, acidified with 2N hydrochloric acid, and extracted with ethyl acetate. The ethyl acetate layer is washed with water, and with 2N sodium carbonate twice. The alkaline layer is acidified with 2N hydrochloric acid and the resulting acidic layer is extracteed with ethyl acetate. The extract is washed with water, dried and concentrated under reduced pressure to give crude crystals, which is recrystallized from 169 mg of the compound (2) in 88% yield as colorless prismatic crystals. Mp. 190° C. to 192° C.

Anal. Calcd. (%) for $C_{23}H_{30}O_5$: C 71.47, H 7.82, Found (%): C 71.23, H 7.76.

The compound (7-3) to (7-6) shown in Table 3 are prepared in the same manner.

EXAMPLE 8

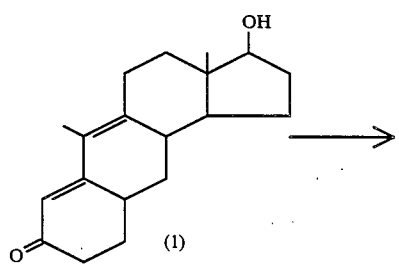

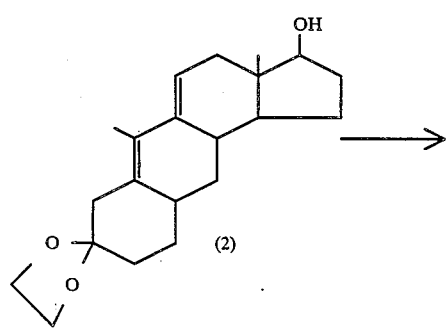

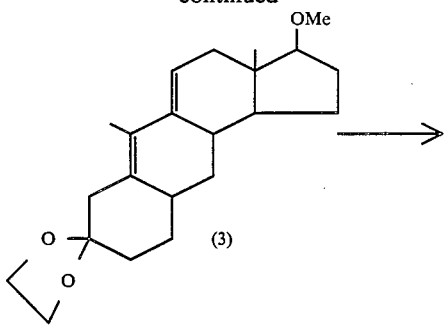

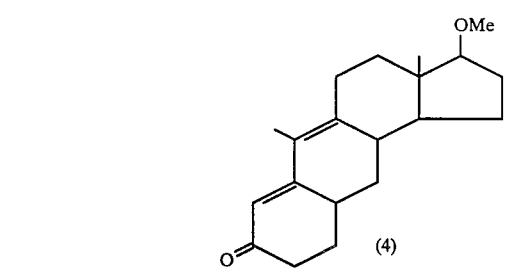

(1) Same as the compound (4) in Example 3
(2) 8,8-ethylenedioxy-3β-hydroxy-3aβ,6-dimethyl-2,3,3a,4,7,8,9,10,10aβ,11,11aβ,11bα-dodecahydro-1H-cyclopenta-[a]anthracene
(3) 8,8-ethylenedioxy-3β-methoxy-3aβ,6-dimethyl-2,3,3a,4,7,8,9,10,10aβ,11,11aβ,11bα-dodecahydro-1H-cyclopenta[a]anthracene
(4) 3β-methoxy-3aβ,6-dimethyl-2,3,3a,4,5,8,9,10,-10aβ,11,11aβ,11bα-dodecahydro-1H-cyclopenta[a]anthracen-8-one (i) To a solution of 5.0 g of the compound (1) in 160 ml of dry benzene are added 14 ml of ethylene glycol and 880 mg of pyridinium p-toluenesulfonate and the mixture is refluxed for 3 hours in a flask equiped with a dehydrating tower in which silica gel (blue, middle particle size) is packed. After cooling, the reaction mixture is poured into chilled water. The benzene layer is washed with water, dried, and concentrated under reduced pressure. The residue is chromatographed [silica gel, Merck, Lobar C. eluted with benzene—ethyl acetate (2:1)]to give 4.64 g of the compound (2) in 80% yield as a colorless powder.

NMRδ ppm(CDCl₃): 0.72(3H,s), 1.80(3H,s), 3.74(1H,t,J=8 Hz), 3.94(4H,s), 5.60(1H,brs).

IRν max (CHCl₃)cm⁻¹: 3595, 3440, 1075, 1037.

(ii) To 3.4 g of sodium hydride (oil, 50%) which is washed with pentane three times beforehand and dried under a nitrogen atmosphere is added a solution of 2.3 g of compound (2) prepared above in 70 ml of dry tetrahydrofuran and the mixture is stirred at 55° C. for 1 hour. After the reaction mixture is cooled, 7.0 ml of methyl iodide is added. The mixture is stirred at room temperature for 48 hours. The reaction mixture is concentrated under reduced pressure and then ether is added to the residue. The remaining reagent is decomposed with a saturated aqueous solution of ammonium chloride under ice cooling. The ether layer is washed with water and a saturated aqueous solution of sodium chloride, dried over sodium sulfate, and concentrated under reduced pressure. The residue is chromatographed [silica gel, Merck, Lobar C, eluted with cyclohexane—ethyl acetate (9:1)]to give 1.90 g of the oily compound (3) in 79% yield.

NMRδ ppm(CDCl3): 0.72(3H,s), 1.79(3H,s), 3.34(3H,t,J=8 Hz), 3.35(3H,s), 3.95(4H,s), 5.59(1H,brs).

(iii) To a solution of 1.90 g of the compound (3) prepared above in 100 ml of acetone is added 2.0 ml of conc. hydrochloric acid and the mixture is stirred at room temperature for 30 minutes. The reaction mixture poured into chilled water is extracted with dichloromethane. The extract is successively washed with water, 5% aqueous solution of sodium hydrogencarbonate, and water, dried, and concentrated under reduced pressure. The residue is chromatographed [silica gel, Merck, Lobar C, eluted with cyclohexane—ethyl acetate (4:1)] to give 1.53 g of the oily compound (4) in 93% yield.

IRν max(CHCl3)cm$^{-1}$: 1647, 1590, 1574.

EXAMPLE 9

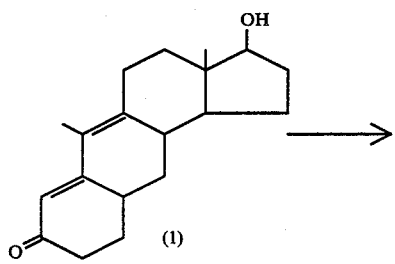

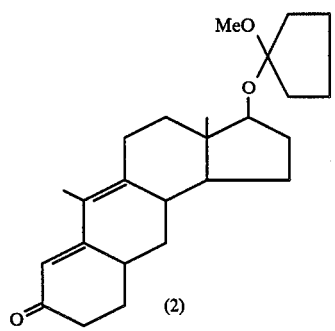

(1) Same as the compound (4) in Example 3

(2) 3β-(1-methoxycyclopentyloxy)-3aα,6-dimethyl-2,3,3a,4,5,8,9,10,10aβ,11,11aβ,11bα-dodecahydro-1H-cyclopenta[a]anthracen-8-one To 5 ml of 1-methoxycyclopentene is added 500 mg of the compound (1) and 10 mg of pyridinium p-toluenesulfonate is added to the suspension at 0° C. and the mixture is stirred at the same temperature for 30 minutes. The reaction mixture diluted with 20 ml of hexane—benzene (1:1) is applied to the column on alumina (Merck, 5 g) and eluted with 50 ml of benzene. The eluate is concentrated under reduced pressure. The residue is further chromatographed [30 g of alumina, eluted with hexane—benzen (1:1)] to give 502 mg of the compound (2) as a colorless oil in 75% yield.

IRν max(CCl4)cm$^{-1}$: 1666, 1585, 1575.

EXAMPLE 10

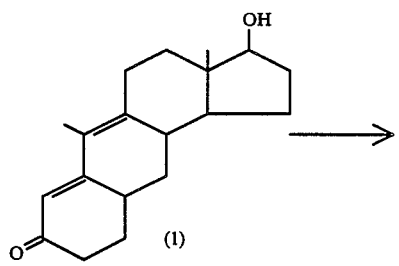

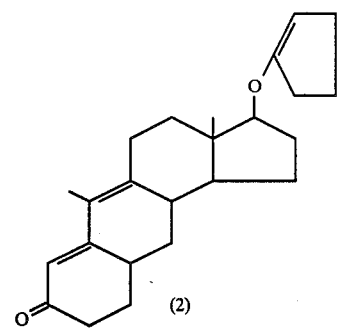

(1) Same as the compound (4) in Example 3.

(2) 3β-(1-cyclopentenyloxy)-3aβ,6-dimethyl-2,3,3a,4,5,8,9,10,10aβ,11,11aβ,11bα-dodecahyro-1H-cyclopenta[a]anthracen-8-one The reaction shown in Example 9 is carried out at room temperature for 2 hours and the reaction mixture is treated in the same manner. The prepared product is crystallized from a mixture of hexane—ether to give 362 mg of the compound (2) in 59% yield as colorless plate crystals.

Mp. 129° C. to 130° C.

Anal. Calcd. (%) for $C_{24}H_{32}O_2$: C 81.77, H 9.15, Found (%): C 81.60, H 9.13

EXAMPLE 11

The compounds (11-1) to (11-5) shown in Table 4 can be prepared in the same manner as in Example 8, 9, and 10.

EXAMPLE 12

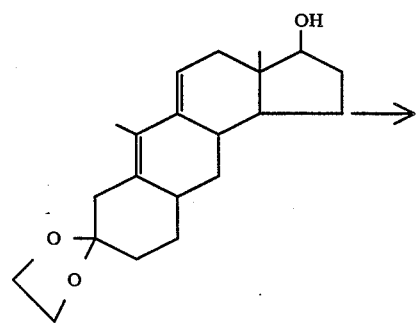

-continued

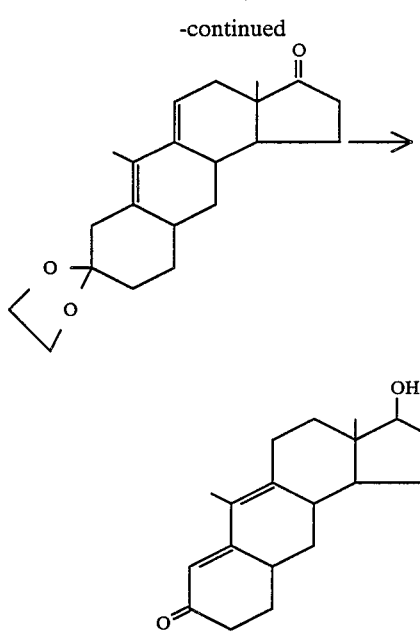

(1) Same as the compound (2) in Example 8
(2) 8,8-ethylenedioxy-3aβ, 6-dimethyl-2,3,3a,4,7,8,9,10,-10aβ,11,11aβ,11bα-dodecahydro-1H-cyclopenta[a]anthracen-3-one
(3) 3β-hydroxy-3α,3aβ,6-trimethyl-2,3,3a,4,5,8,9,10,-10aβ,11,11aβ,11bα-dodecahydro-1H-cyclopenta[a]anthracen-8-one (i) To a solution of Collins reagent which is prepared from adding 25.2 g of chromic anhydride to a solution of 44 ml of dry pyridine in 400 ml of dichloromethane in a nitrogen atmosphere is added a solution of 13.8 g of the compound (1) prepared in Example 8 in 100 ml of dichloromethane at once under stirring. The mixture is stirred for 10 minutes and then the dichloromethane layer is collected by decantation and concentrated under reduced pressure. The residue dissolved in ether, washed with 2N sodium hydroxide and water, dried over sodium sulfate, and concentrated under reduced pressure. The crude product is crystallized with ether to give 4.01 g of the compound (2) in 58% yield as colorless prisms. Mp. 157° C. to 158.5° C.

NMRδ ppm(CDCl$_3$): 0.86(3H,s), 1.80(3H,s), 3.94(4H,s), 5.62(1H,brs).

IRν max(Nujol)cm$^{-1}$: 1740.

(i) To a solution of 4.0 g of the compound (2) in 70 ml of dry ether is added 18.3 ml of solution of methylmagnesium bromide in ether (about 1 mol solution. Tokyo Kasei Kogyo Co., Ltd.) under ice cooling with stirring over 20 minutes. The mixture is stirred at room temperature for 3 hours and then the remaining Grignard reagent is decomposed with a saturated aqueous solution of ammonium chloride. The mixture is extracted with ether and the ether layer is washed with water, dried, and concentrated to give colorless oil. The resulting oil is dissolved in 100 ml of acetone and 2 ml of 6N hydrochloric acid is added thereto. The mixture is stirred at room temperature for an hour. After neutralizing with 2N sodium carbonate, the reaction mixture is concentrated under reduced pressure. The residue added water is extracted with dichloromethane. The dichloromethane layer is washed with water, dried, and concentrated under reduced pressure. The residue is chromatographed [silica gel, Merck, Lobar C. eluted with benzene—ethyl acetate (2:1)] to give crude crystals, which is crystallized from a mixture of ether—petroleum ether to give 2.15 g of the compound (3) in 59% yield as colorless prismatic crystals. Mp. 175° C. to 177° C.

Anal. Calcd. (%) for C$_{20}$H$_{28}$O$_2$: C 79.95, H 9.39, Found (%): C 79.99, H 9.24.

The physical constants are shown in Table 5.

EXAMPLE 13

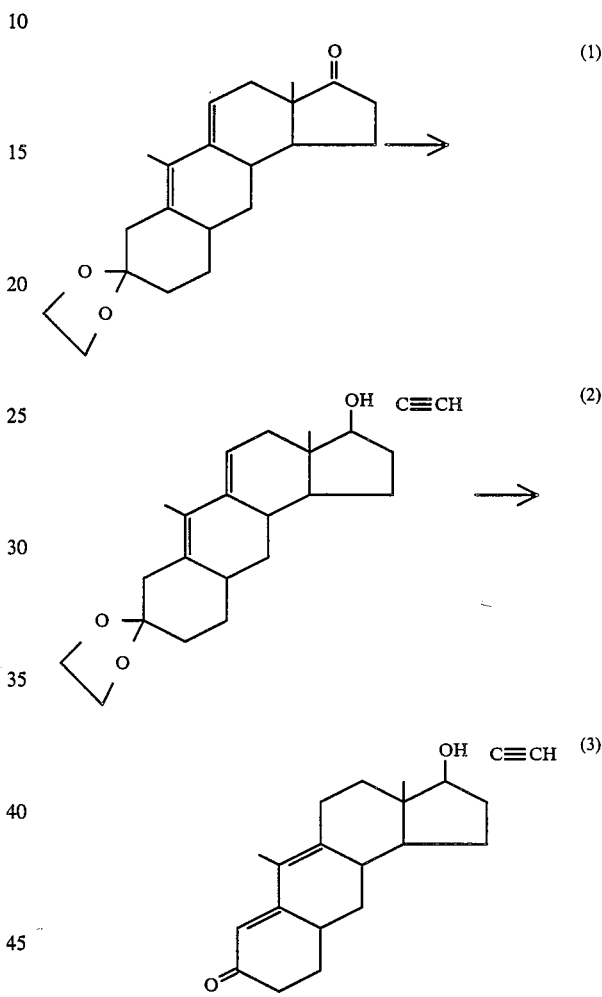

(1) Same as the compound (2) in Example 12
(2) 8,8-ethylenedioxy-3α-ethynyl-3β-hydroxy-3aβ,6-dimethyl-2,3,3a,4,7,8,9,10,10aβ11,11 aβ,11bα-dodecahydro-1H-cyclopenta[a]anthracene
(3) 3α-ethynyl-3β-hydroxy-3aβ,6-dimethyl-2,3,3a,4,5,8,9,10,10aβ,11,11aβ,11bα-dodecahydro-1H-cyclopenta[a]anthracen-8-one (i) To a solution of 2.40 g of trimethylsilylacethylene in 30 ml of dry tetrahydrofuran is added 15 ml of solution of 1.6N n-butyllithium in hexane at 0° C. in a nitrogen atmosphere and the mixture is stirred at the same temperature for 30 minutes. To the resulting solution is added a solution of 800 mg of the compound (1) prepared above in 20 ml of dry tetrahydrofuran over 10 minutes and the mixture is stirred at 0° C. for 30 minutes. The reaction mixture to which is added a saturated aqueous solution of ammonium chloride is extracted with ether. The ether layer is washed with water, dried and concentrated under reduced pressure to give 1.13 g of oil. To a solution of this oil in 30 ml of dry tetrahydrofuran is added 1.36 g of tetraethylammonium fluoride (dihydrate) at room temperature under stirring and the mixture is stirred for 10 minutes. The reaction mixture, to which is added water, is extracted with dichloromethane. The extract is washed with water, dried, and concentrated under reduced pressure. The residue is chromatographed [silica gel, Merck, Lobar B, eluted with cyclohexane—ethyl acetate (6:1)] to give 837 mg of the oil compound (2) in 97% yield.

NMRδppm(CDCl$_3$): 0.82(3H,s), 1.80(3H,s), 2.55(1H,s), 4.28(4H,s), 5.66(1H,brs).

(ii) To a solution of 837 mg of the compound (2) prepared above in 40 ml of acetone is added 0.8 ml of conc. hydrochloric acid and the mixture is stirred for 30 minutes. The reaction mixture to which is added 1 ml of pyridine is concentrated under reduced pressure. The residue dissolved in ether is washed with water, dried, and concentrated under reduced pressure. The residue is chromatographed under reduced pressure. The residue is chromatographed [silica gel, Merck, Lobar B, eluted with cyclohexane—ethyl acetate (2:1)] to give crude crystals, which is crystallized from ether—pentane to give 698 mg of the compound (3) in 95% yield as an prisms. Mp. 170° C. to 172° C.

Anal. Calcd. (%) for C$_{21}$H$_{26}$O$_2$: C 81.25, H 8.44, Found (%): C 81.24, H 8.37.

The compound (13-4) shown in Table 5 can be prepared in the same manner.

(1) Same as the compound (2) in Example 12
(2) 8,8-ethylenedioxy-2-hydroxymethylene-3aβ,6-dimethyl-2,3,3a,4,7,8,9,10,10aβ,11,11aβ,11bα-dodecahyro-1H-cyclopenta[a]anthracen-3-one
(3) 8,8-ethylenedioxy-3β-hydroxy-2β-hydroxymethyl-3aβ,6-dimethyl-2,3,3a,4,7,8,9,10,10aβ,11,11aβ,11bα-dodecahydro-1H-cyclopenta[a]anthracene
(4) 8,8-ethylenedioxy-3β-hydroxy-2α-hydroxymethyl-3aβ,6-dimethyl-2,3,3a4,7,8,9,10,10aβ,11,11aβ,11bα-dodecahydro-1H-cyclopenta[a]anthracene
(5) 3β-hydroxy-2β-hydroxymethyl-3aβ,6-dimethyl-2,3,3a4,5,8,9,10,10aβ,11,11aβ,11bα-dodecahydro-1H-cyclopenta[a]anthracen-8-one
(6) 3β-hydroxy-2α-hydroxymethyl-3aβ,6-dimethyl-2,3,3a,4,5,8,9,10,10aβ,11,11,aβ,11bα-dodecahydro-1H-cyclopenta[a]anthracen-8-one (i) To a solution of 3.41 g of the compound (1) in 70 ml of dry benzene and 5 ml of dimethylsulfoxide are added 10.5 ml of ethyl formate and 1.25 g of sodium hydride (oil, 50%) at 10° C. and the mixture is stirred for 2 hours. The reaction mixture which is allowed to stand at room temperature overnight is diluted with 300 ml of benzene and water is added to separate. The alkaline aqueous layer is acidified with 0.5N sulfuric acid. The precipitated crystals are collected by filtration and washed with water three times. The crystals are recrystallized from acetone to give 3.39 g of the compound (2)

EXAMPLE 14

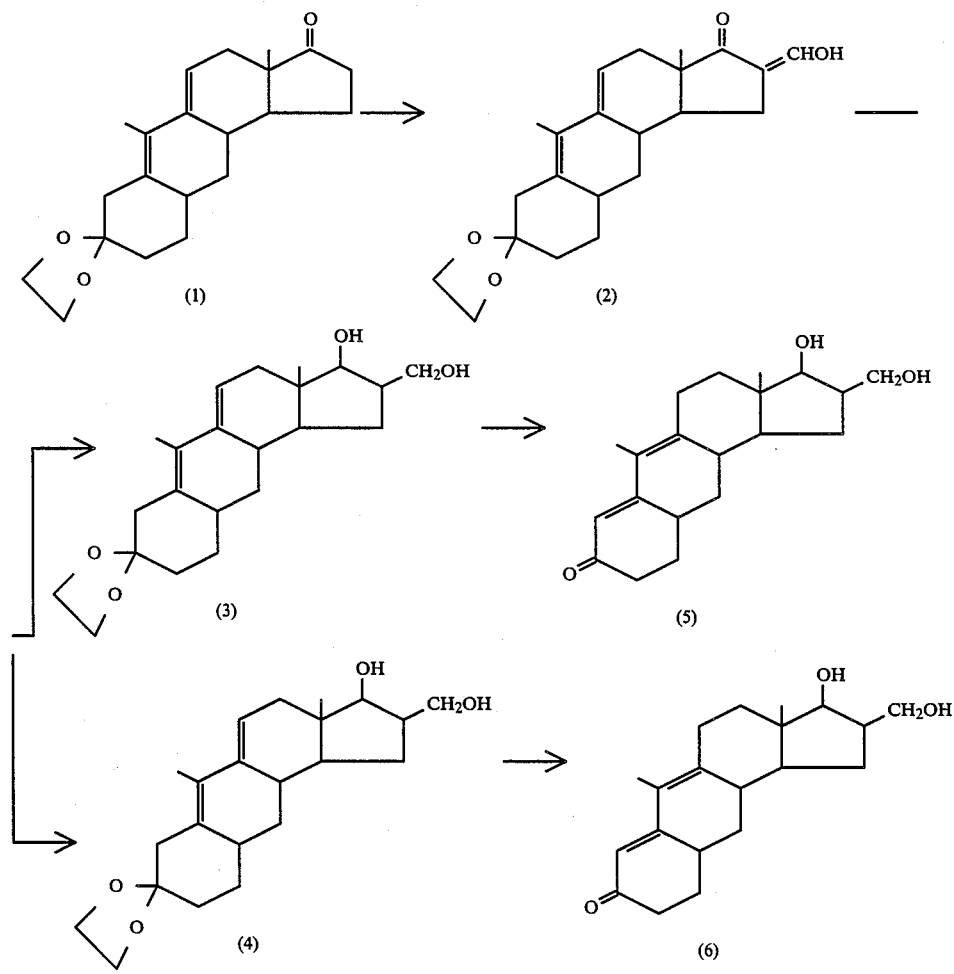

in 92% yield as colorless powder. Mp. 229° C. to 232° C. (decomposed).

IRν max(Nujol)cm⁻¹: 1688, 1630, 1562.

(ii) To a suspension of 3.34 g of the compound (2) prepared above in 90 ml of ethanol and 30 ml of tetrahydrofuran is added 1.04 g of sodium borohydride. After stirring at room temperature for 6 hour, the reaction mixture is concentrated under reduced pressure till the volume becoming half. The concentrated reaction mixture to which is added water is extracted with chloroform. The chloroform layer is washed with water, dried, and concentrated under reduced pressure. The residue is chromatographed [50 g of silica, gel, chloroform—ethyl acetate (4:1)] and the nonpolar fraction is crystallized from a mixture of acetone and n-hexane to give 920 mg of the compound (3) in 27% yield as colorless prisms. Mp. 174° C. to 177° C.

NMRδ ppm(CDCl₃): 0.79(3H,s), 1.81(3H,s), 3.98(4H,s), 4.00(1H,d,J=9 Hz), 5.64(1H,brs).

The polar fraction is crystallized from a acetone and n-hexane to give 2.27 g of the compound (4) in 67% yield as colorless prisms. Mp. 203° C. to 205° C.

NMRδ ppm(CDCl₃): 0.78(3H,s), 3.50~3.83(3H,m), 3.97(4H,s), 5.63(1H,brs).

(iii) To a solution of 900 mg of the compound (3) prepared above in 40 ml of acetone is added 6.0 ml of 2N hydrochloric acid and the mixture is stirred at room temperature for 3.5 hour. The reaction mixture is poured to chilled water and extracted with chloroform. The chloroform layer is washed with water, dried, and concentrated under reduced pressure. The residue is chromatographed (8 g of silica gel) and the fraction eluted with chloroform—acetone (9:1) is crystallized with acetone to give 707 mg of the compound (5) in 90% yield as colorless needle crystals. Mp. 121° C. to 125° C.

NMRδ ppm(CDCl₃): 0.97(3H,s), 1.85(3H,s), 3.55~4.05(3H,m), 6.01(1H,s).

IRν max(Nujol)cm⁻¹: 3335, 1630, 1571, 1566.

(iv) The corresponding compound (4) is prepared from the compound (6) in the same manner as in above mentioned (iii). Colorless prisms. Mp. 185° C. to 187° C.

NMRδ ppm(CDCl₃): 0.96(3H,s), 3.47(3H,s), 3.47(1H,d,J=7 Hz), 3.60~3.90(2H,m), 6.00(1H,s).

IRν max(Nujol)cm⁻¹: 3400, 3325, 1632, 1581, 1555.

Anal. Calcd. (%) for $C_{20}H_{28}O_3$: C 75.91, H 8.92, Found (%): C 75.66, H 8.84.

EXAMPLE 15

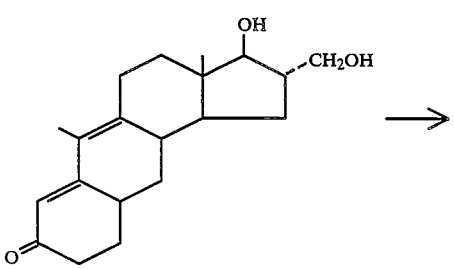

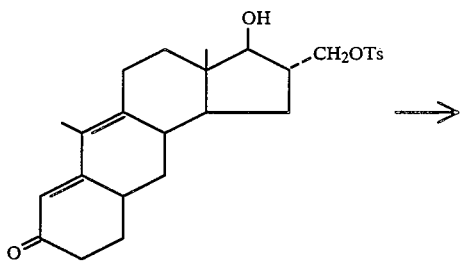

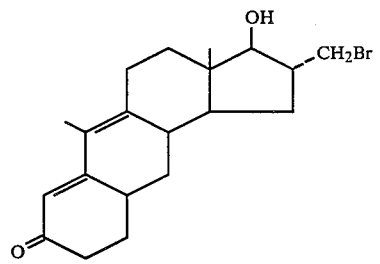

(1) Same as the compound (6) in Example 14
(2) 3β-hydroxy-3aβ,6-dimethyl-2α-(p-toluenesulfonyloxymethyl)-2,3,3a,4,5,8,9,10,10aβ,11,11aβ,1-1bα-dodecahydro-1H-cyclopenta[a]anthracen-8-one
(3) 2α-bromomethyl-3β-hydroxy3aβ,6-dimethyl-2,3,3a,4,5,8,9,10,10aβ,11,11aβ,11,11aβ,11bα-dodecahydro-1H-cyclopenta[a]anthracen-8-one (i) To a solution of 650 mg of the compound (1) prepared above in 10 ml of chloroform are added 1.0 ml of dry pyridine and 1.0 g of p-toluenesulfonyl chloride at 0° C. and the mixture is stirred at room temperature for 5 hours. The reaction mixture to which is added 1 ml of water is stirred vigorously for 30 minutes and then extracted with chloroform. The chloroform layer is washed with 1N sodium carbonate and water, dried, and concentrated under reduced pressure. The residue is chromatographed [silica gel, Merck, benzene—ethyl acetate (1:1) to give 620 mg of tosylate as a colorless powder in 64% yield.

NMRδ ppm(CDCl₃): 0.90(3H,s), 1.82(3H,s), 2.43(3H,s), 3.38(1H,d,J=8 Hz), 4.10(2H,d,j=5 Hz), 5.99(1H,s), 7.36(2H,d,J=8 Hz), 7.80(2H,d,J=8 Hz).

(ii) To a solution of 620 mg of tosylate (2) prepared above in 10 ml of dry acetone is added 500 mg of lithium bromide (anhydrous) in a nitrogen atmosphere and the mixture is refluxed for 16 hours. The reaction mixture is concentrated under reduced pressure. The residue which is added water is extracted with dichloromethane and the dichloromethane layer is washed with water, dried over anhydrous sodium sulfate, and concentrated under reduced pressure. The residue is chromatographed [silica gel, Merck, Lobar B, n-hexane—ethyl acetate (2:3)] to give 420 mg of the powder compound (3) in 84% yield.

NMRδ ppm(CDCl₃): 0.94(3H,s), 3.37~3.74(3H,m), 6.00(1H,s).

IRν max(CHCl₃)cm⁻¹: 3430, 1642, 1590, 1574.

EXAMPLE 16

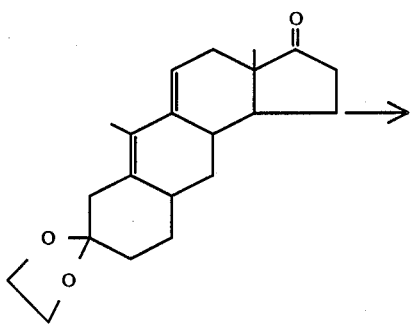

(1)

(2)

(1) Same as the compound (2) in Example 12
(2) 2β-ethyl-8,8-ethylenedioxy-3aβ,6-dimethyl-2,3,3a,4,7,8,9,10,10aβ,11,11aβ,11bα-dodecahydro-1H-cyclopenta[a]anthracen-3-one To a solution of lithium diisopropylamide prepared from adding 1.48 ml of 1.6N n-butyllithium in hexane to a solution of 0.3 ml of diisopropylamine in 8 ml of dry tetrahydrofuran is added a solution of 650 mg of the compound (1) in 10 ml of dry tetrahydrofuran at −78° C. in a nitrogen atmosphere under stirring over 15 minutes. The mixture is stirred at the same temperature for 30 minutes and then 0.6 ml of hexamethylphosphoric triamide and 0.5 ml of ethyl iodide are added. The resulting mixture is slowly warmed and stirred at 0° C. for 2 hours. The reaction mixture is poured into chilled water and extracted with ether. The ether layer is washed with water, dried, and evaporated under reduced pressure. The oily residue is dissolved in 8 ml of methanol and 1.0 ml of 2N aqueous solution of sodium hydroxide is added thereto and the mixture is refluxed in a nitrogen atmosphere for 1 hour. After cooling, the reaction mixture, to which is added water is extracted with ether. The extract is washed with water, dried and concentrated under reduced pressure. The residue is chromatographed [silica gel, Merck, Lobar B, eluted with benzene—ethyl acetate (9:1)] to give crude crystal, which is crystallized from ether to give 305 mg of the compound (2) in 43% yield as colorless prisms.

Mp. 139° C. to 141° C.

Anal. Calcd. (%) for $C_{23}H_{32}O_2$: C 77.49, H 9.05, Found (%): C 77.26, H 8.89.

The physical constants are shown in Table 6.

EXAMPLE 17

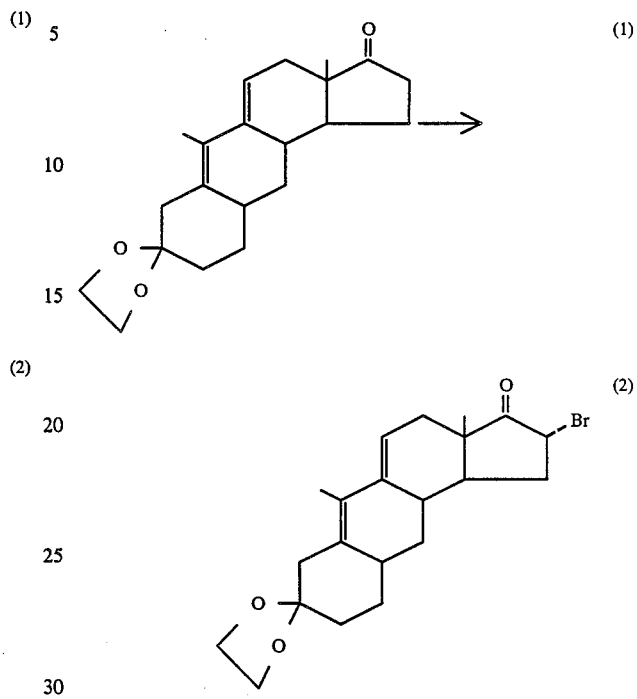

(1)

(2)

(1) Same as the compound (2) in Example 12
(2) 2α-bromo-8,8-ethylenedioxy-3aβ,6-dimethyl-2,3,3a,4,7,8,9,10,10aβ,11,11aβ,11bα-dodecahydro-1H-cyclopenta[a]anthracen-3-one To a solution of lithium diisopropylamide which is prepared from dropwise adding 7.8 ml of 1.6N solution of n-butyllithium in hexane to a solution of 1.60 ml of diisopropylamine in 25 ml of dry tetrahydrofuran is added a solution of 3.00 g of the compound (1) in 25 ml of dry tetrahydrofuran in a nitrogen atmosphere at −78° C. over 20 minutes under stirring. The mixture is stirred at the same temperature for 1 hour and then a solution of 1.61 g of bromine in 10 ml of dichloromethane is added thereto. After 10 minutes, 6 ml of saturated aqueous solution of sodium hydrogencarbonate is added thereto and then the mixture is concentrated under reduced pressure till it becomes ⅓ volume. The concentrate is extracted with ether and the ether layer is washed with water and a saturated aqueous solution of sodium chloride, dried over sodium sulfate, and concentrated under reduced pressure. The residue is passed through a short column on silica gel eluting with 150 ml of hexane—ethyl acetate (2:1). After the solvent is evaporate, the residue is crystallized from methanol to give 3.02 g of the compound (2) in 81% yield as colorless prisms.

Mp. 145° C. to 150° C.

The physical constants are shown in Table 6.

EXAMPLE 18

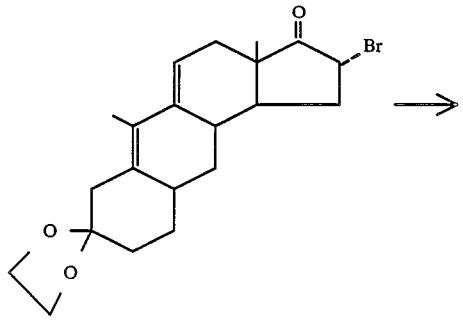 (1)

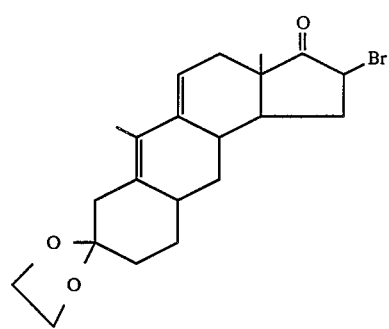 (2)

(1) Same as the compound (2) in Example 17
(2) 2β-bromo-8,8-ethylenedioxy-3aβ,6-dimethyl-2,3,3a,4,7,8,9,10,10aβ,11,11aβ,11bα-dodecahydro-1H-cyclopenta[a]anthracen-3-one To a solution of 400 mg of the compound (1) in 10 ml of dry dimethylformamide in a nitrogen atmosphere is added 1.3 g of lithium bromide (anhydrous) and the mixture is stirred at room temperature for 48 hours. The reaction mixture poured into water is extracted with ether. The ether layer is washed with water, dried, and concentrated under reduced pressure. The residue is chromatographed [silica gel, Merck, Lobar B, eluted with hexane ethyl acetate (4:1)] to give 280 mg of the compound (2) as a pale yellow powder in 70% yield.

The physical properties are shown in Table 6.

EXAMPLE 19

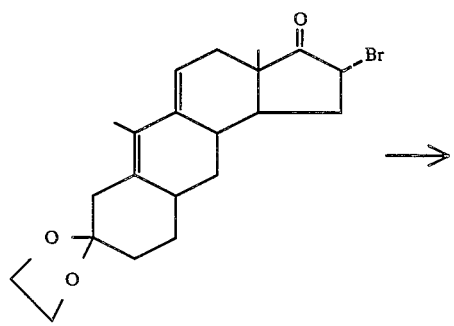 (1)

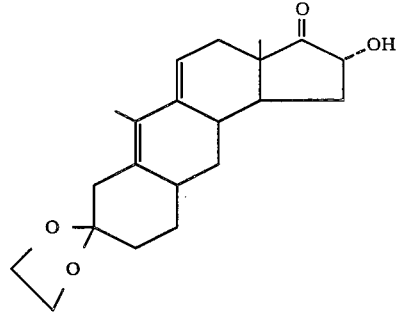 (2)

(1) Same as the compound (2) in Example 17
(2) 8,8-ethylenedioxy-2α-hydroxy-3aβ,6-dimethyl-2,3,3a,4,7,8,9,10,10aβ,11,11aβ,11bα-dodecahydro-1H-cyclopenta[a]anthracen-3-one To a solution of 770 mg of the compound (1) in 10 ml of 80% aqueous solution of dimethylformamide is added 1.2 ml of 2N aqueous solution of sodium hydroxide at 10° C. and the mixture is stirred for 45 minutes. The reaction mixture, to which is added 30 ml of chilled water is extracted with ethyl acetate. The ethyl acetate is washed with water and a saturated aqueous solution of sodium chloride, dried, and concentrated under reduced pressure. The residue is chromatographed [silica gel, Merck, Lobar B, eluted with hexane—ethyl acetate (3:1)] to give 434 mg of the compound (2) as a colorless powder in 67% yield.

The physical properties are shown in Table 6.

EXAMPLE 20

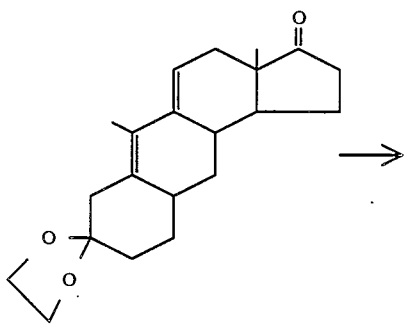 (1)

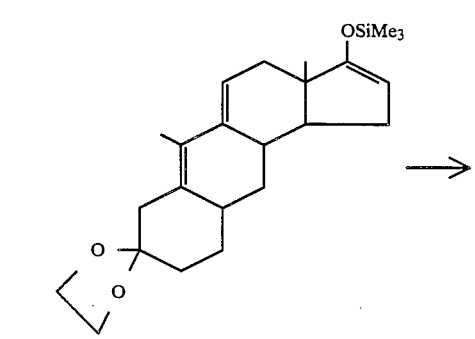 (2)

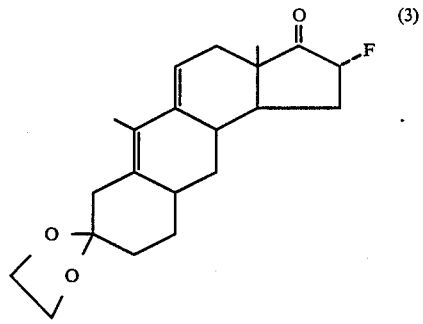

(1) Same as the compound (2) in Example 12
(2) 8,8-ethylenedioxy-3aβ,6-dimethyl-3-trimethyl-silyloxy-3a,4,7,8,9,10,10aβ,11,11aβ,11bα-decahydro-1H-cyclopenta[a]anthracene
(3) 8,8-ethylenedioxy-2α-fluoro-3aβ,6-dimethyl-2,3,3a,4,7,8,9,10,10aβ,11,11aβ,11bα-dodecahydro-1H-cyclopenta[a]anthracen-3-one (i) The corresponding silyl ether (2) is prepared from the compound (1) in the same manner as in Example 3-(ii).

Colorless oil.

NMRδ ppm(CDCl₃): 0.15(9H,s), 0.90(3H,s), 1.84(3H,s), 3.92(4H,s), 5.65(1H,brs), 5.70(1H,s).

(ii) To a solution of 1.03 g of the silyl ether (2) prepared above in 10 ml of dry acetonitrile is added 398 mg of xenon deflouride under ice cooling and the mixture is stirred at room temperature for 30 minutes. The reaction mixture poured into chilled water is extracted with dichloromethane. The dichloromethane layer is successively washed with 1% aqueous solution of sodium hydrogencarbonate, water, and a saturated aqueous solution of sodium chloride, dried, and concentrated under reduced pressure. The residue is chromatographed [silica gel, Merck, Lobar B, eluted with cyclohexane—ethyl acetate (4:1)] to give crude crystals, which is recrystallized from a mixture of acetone and hexane to give 266 mg of the compound (3) in 30% yield as pale yellow needle crystals. Mp. 200° to 202° C.

The physical properties are shown in Table 6.

EXAMPLE 21

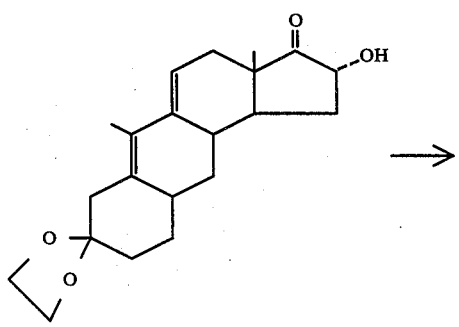

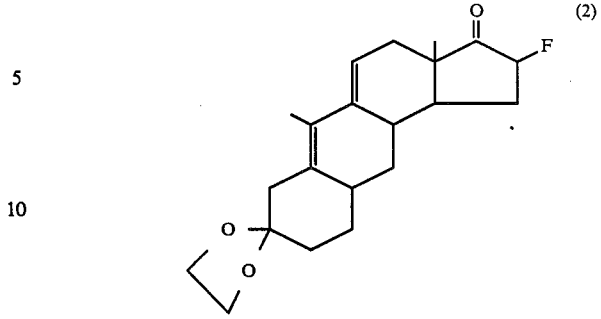

(1) Same as the compound (2) in Example 19
(2) 8,8-ethylenedioxy-2β-fluoro-3aβ,6-dimethyl-2,3,3a,4,7,8,9,10,10aβ,11,11aβ,11bα-dodecahydro-1H-cyclopenta[a]anthracene-3-one To a solution of 800 mg of the compound (1) prepared in Example 19 in 20 ml of dichloromethane are added 1.0 ml of 2,6-lutidine and 0.6 ml of trifluoromethanesulfonic anhydride with stirring under ice cooling and the mixture is stirred at the same temperature for 40 minutes. The reaction mixture poured into chilled water is extracted with dichloromethane. The dichloromethane layer is successively washed with water, 3% copper sulfate, and water, dried, and evaporated under reduced pressure. Then, to a solution of resulting powdery residue in 12 ml of dry tetrahydrofuran is added 2.1 ml of solution of tetra-n-butylammonium fluoride in tetrahydrofuran (1M) and the mixture is stirred for 30 minutes. The reaction mixture, to which is added water is extracted with dichloromethane. The extract is washed with 1% aqueous solution of sodium carbonate and water, dried, and concentrated under reduced pressure. The residue is chromatographed [silica gel, Merck, Lobar B, eluted with cyclohexane—ethyl acetate (9:1)] to give the crude crystals, which is recrystallized from a mixture of acetone and hexane to give 362 mg of the compound (2) in 49% yield as colorless column crystals. Mp. 186°–188° C.

[α]$_D$ +250°±9.4° (c=0.309, CHCl₃).

The physical constants are shown in Table 6.

EXAMPLE 22

As the same manner in Examples 16 and 17, the compound (22-1) and (22-2) shown in Table 6 can be prepared.

EXAMPLE 23

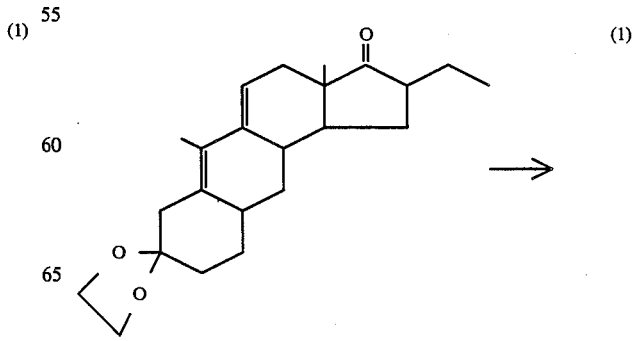

EXAMPLE 24

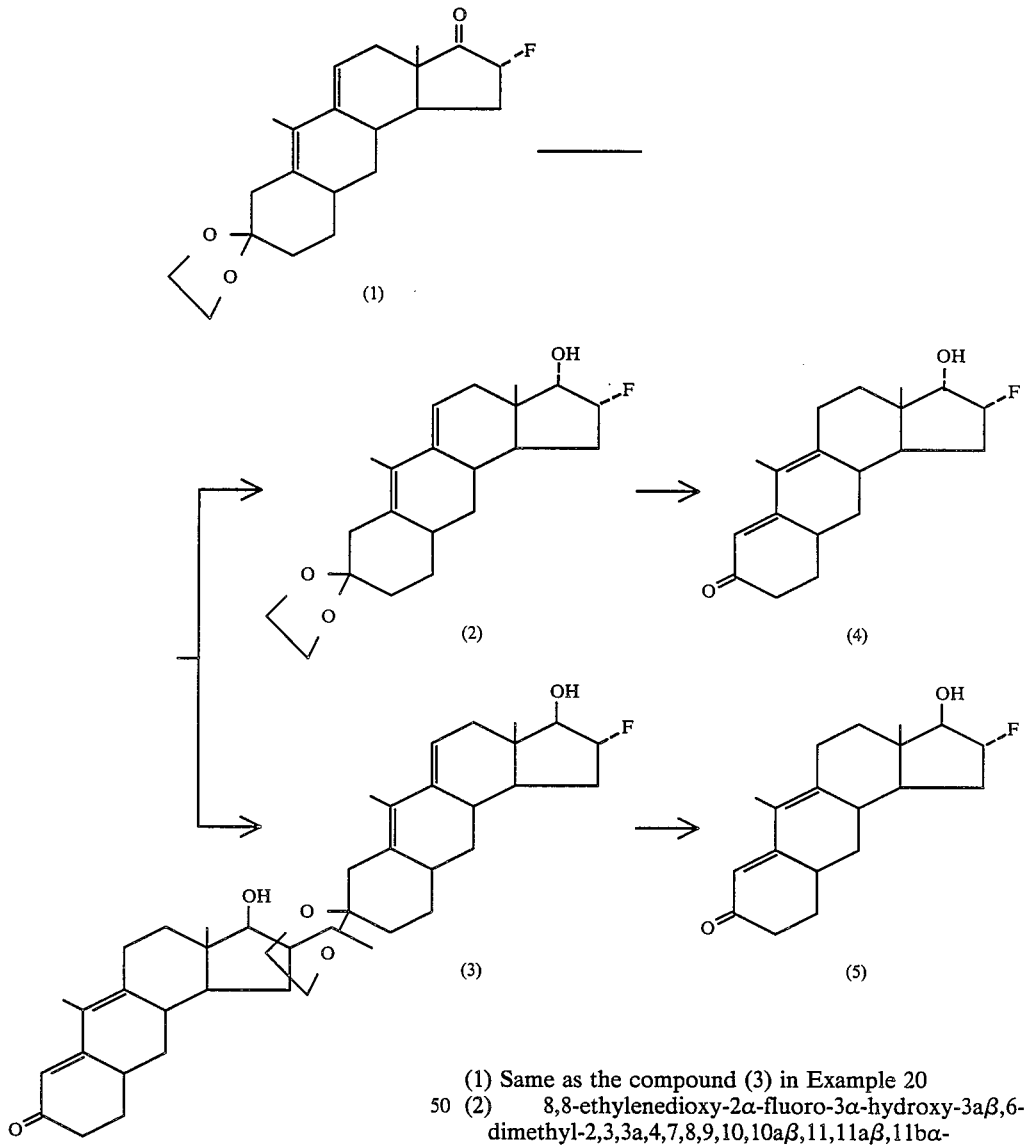

(1) The same as the compound (2) in Example 16
(2) 2β-ethyl-3β-hydroxy-3aβ,6-dimethyl-2,3,3a,4,5,8,9,10,10aβ,11,11aβ,11bα-dodecahydro-1H-cyclopenta[a]anthracen-8-one To a solution of 410 mg of the compound (1) in 6 ml of methanol is added 21 mg of sodium borohydride under ice cooling and the mixture is stirred for 2 hours. The reaction mixture, to which is added water is extracted dichloromethane. The extract is washed with water, dried, and concentrated under reduce pressure. To the prepared residue dissolved in 8 ml of ethanol is added 0.8 ml of 2N hydrochloric acid and the mixture is allowed to stand for 4 hours. The reaction mixture, to which is added water is extracted with dichloromethane. The dichloromethane layer is washed with water, dried over sodium sulfate, and concentrated under reduced pressure. The residue is chromatographed [silica gel, Merck, Lobar B, eluted with cyclohexane—ethyl acetate (3:1)] to give 174 mg of the compound (2) as colorless powder in 48% yield.

The physical constants are shown in Table 7.

(1) Same as the compound (3) in Example 20
(2) 8,8-ethylenedioxy-2α-fluoro-3α-hydroxy-3aβ,6-dimethyl-2,3,3a,4,7,8,9,10,10aβ,11,11aβ,11bα-dodecahydro-1H-cyclopenta[a]anthracene
(3) 8,8-ethylenedioxy-2α-fluoro-3β-hydroxy-3aβ,6-dimethyl-2,3,3a,4,7,8,9,10,10aβ,11,11aβ,11bα-dodecahydro-1H-cyclopenta[a]anthracene
(4) 2α-fluoro-3α-hydroxy-3aβ,6-dimethyl-2,3,3a,4,5,8,9,10,10aβ,11,11aβ,11bα-dodecahydro-1H-cyclopenta[a]anthracen-8-one
(5) 2α-fluoro-3β-hydroxy-3aβ,6-dimethyl-2,3,3a,4,5,8,9,10,10aβ,11,11aβ,11bα-dodecahydro-1H-cyclopenta[a]anthracen-8-one (i) To a solution of 680 mg of the compound (1) in 16 ml of tetrahydrofuran and 12 ml of ethanol is added 72 mg of sodium borohydride at 0° C. and the mixture is stirred for 30 minutes. The reaction mixture poured into water is extracted with dichloromethane. The dichloromethane layer is washed with water, dried, and concentrated. The residue is chromatographed [silica gel, Merck, Lobar B, eluted with benzene—ethyl acetate (9:1)] and the crude crystals obtained from the nonpolar-fraction is recrystallized from a mixture of acetone and hexane to give 350 mg of the compound (2) as colorless prisms in 51% yield. Mp. 156° to 158° C. Colorless prisms.

NMRδ ppm(CDCl$_3$): 0.67(3H,s),1.80(3H,s), 3.85(1H,dd,J=5 and 2 Hz), 3.97(4H,s), 5.29(1H,dm,J=53 Hz), 5.64(1H,brs).

Then, the crude crystals obtained from the polar fraction is recrystallized from a mixture of hexane and acetone to give 288 mg of the compound (3) in 42% yield as colorless prisms.

Mp. 133° to 137° C.

NMRδ ppm(CDCl$_3$): 0.72(3H,s), 1.78(3H,s), 3.88(1H,dd,J=22 and 5 Hz), 3.95(4H,s), 4.96(1H,dm,J=55 Hz), 5.60(1H,brs).

(ii) To a solution of 212 mg of the compound (2) in 6.0 ml of acetone is added 0.3 ml of 4N hydrochloric acid and the mixture is stirred at room temperature for 2.5 hours. The reaction mixture, to which is added water is extracted with dichloromethane. The dichloromethane layer is successively washed with water, 2% aqueous solution of sodium hydrogencarbonate, a saturated aqueous solution of sodium chloride, dried, and concentrated under reduced pressure. The resulting residue is recrystallized from a mixture of dichloromethane and ether to give 148 mg of the compound (4) in 80% yield as colorless crystals. Mp. 162° to 164° C.

The physical constants are shown in Table 8.

(iii) From 160 mg of the compound (3) is prepared 117 mg of the compound (5) in the same manner as mention above in 84% yield as colorless prisms. Mp. 152° C. to 154° C.

The physical constants are shown in Table 7.

EXAMPLE 25

The compounds shown in Tables 7 and 8 can be prepared in the same manner as in Examples 23 and 24.

EXAMPLE 26

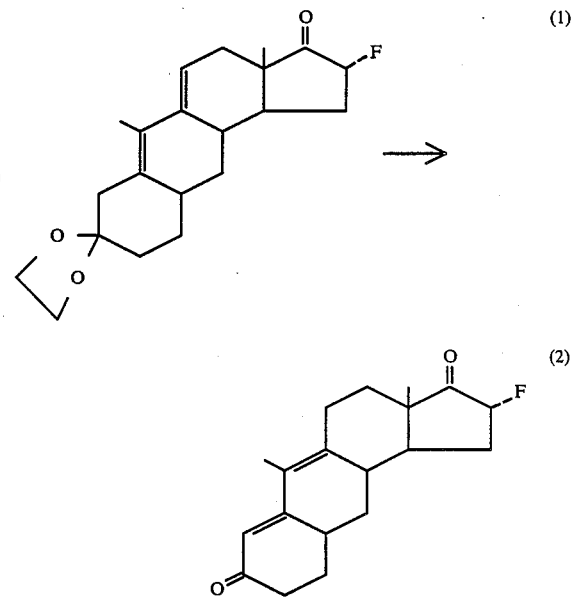

(1) Same as the compound (3) in Example 20

(2) 2α-fluoro-3aβ,6-dimethyl-2,3,3a,4,5,8,9,10,10aβ,11,-11aβ,11bα-dodecahydro-1H-cyclopenta[a]anthracen-3,8-dione To a solution of 90 mg of the compound (1) in 6.0 ml of acetone is added 0.3 ml of 4N hydrochloric acid and the mixture is stirred at room temperature for 3 hours. The reaction mixture to which is added water is extracted with dichloromethane. The dichloromethane layer is successively washed with water, 2% aqueous solution of sodium hydrogencarbonate, and a saturated aqueous solution of sodium chloride, dried, and concentrated under reduced pressure. The residue is chromatographed [silica gel, Merck, Lobar A, eluted with benzene—ethyl acetate (4:1)]. The resulting crystals are recrystallized from methanol to give 51 mg of the compound (2) as colorless prisms in 65% yield. Mp. 170° C. to 172° C.

NMRδ ppm(CDCl$_3$): 1.06(3H,s), 1.87(3H,s), 5.15(1H,ddd,J=52,5.5 and 3 Hz), 6.02(1H,s).

IRν max(Nujol) cm$^{-1}$: 1757, 1650, 1578, 1560, 1321, 1257.

[α]$_D$ −84.0±4.0° (c=0.307CHCl$_3$).

TABLE 1

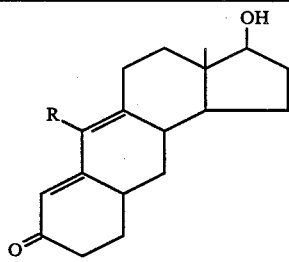

| Compound No.* | R | Mp. °C. | [α]$_D$ | UV λ$_{max}^{EtOH}$ nm | IR ν$_{max}^{Nujol}$ cm$^{-1}$ | NMR δ ppm (CDCl$_3$) |
|---|---|---|---|---|---|---|
| 3-5 | H | 156~158 | −306.0 ± 1.6* (C = 0.520; CHCl$_3$) | 295(ε = 29300) | 3482, 3452, 1651, 1642, 1617, 1589, 1328, 1260, 1206, 1079, 1048, 910, 891. | 0.88 (3H,s), 3.69 (3H,t,J=8Hz), 5.73 (1H,s), 6.05 (1H,s) |
| | | | −295.8 ± 6.1* | | 3440, 1644, 1599, 1570, 1336, | 0.88 (3H,s), 1.82 (3H,t,J=1.5Hz), 3.67 |

TABLE 1-continued

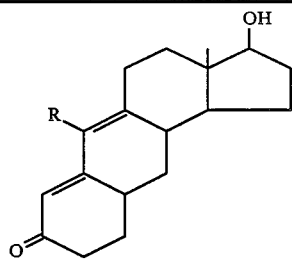

| Compound No.* | R | Mp. °C. | $[\alpha]_D$ | UV $\lambda_{max}^{EtOH}$ nm | IR $\nu_{max}^{Nujol}$ cm$^{-1}$ | NMR δ ppm (CDCl$_3$) |
|---|---|---|---|---|---|---|
| 3-4 | Me | 149~150 | (C = 0.548; CHCl$_3$) | 303(ε = 28200) | 1280, 1265, 1214, 1100, 1065, | (1H,m), 5.99 (1H,s) |
| 3-6 | Et | oil | −267.3 ± 3.0* (C = 1.010; CHCl$_3$) | 302.5(ε = 23500) | 3580, 3400, 1632, 1564, 1327, 1260, 1081, 1000, 866 (CHCl$_3$φ) | 0.90 (3H,s), 0.96 (3H,t,J=7Hz), 2.34 (2H,q,J=7Hz), 3.68 (1H,t,J=8Hz), 6.03 (1H,brs) |

*The number of the left side corresponds to the example number and the right side is the compound number in the said example. Hereinafter the same description is used.

TABLE 2

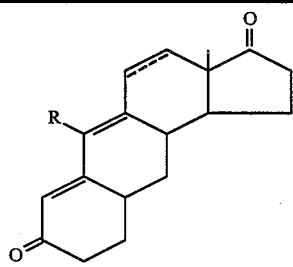

| Compound No | R | Mp. °C. | $[\alpha]_D$ | IR $\nu_{max}^{Nujol}$ cm$^{-1}$ | NMR δ ppm (CDCl$_3$) |
|---|---|---|---|---|---|
| 6-3 | H | 187~189 | −143.6 ± 3.6* (C = 0.512,CHCl$_3$) | 1732, 1660, 1622, 1584, 1324, 1260, 1200, 1060, 928, 912 | 1.02 (3H,s), 5.73 (1H,s), 6.07 (1H,s) |
| 6-2 | Me | 178~181 | −117.7 ± 3.1* (C = 0.510, CHCl$_3$) | 1732, 1653, 1577, 1560, 1328, 1261, 1208, 1062, 1030, 965, 870 | 1.01 (3H,s), 1.86 (3H,d,J=2Hz), 6.02 (1H,s) |
| 6-4 | Me Δ$^4$ | 259~262 | −105.8 ± 4.6* (C = 0.315,CHCl$_3$) | 1725, 1642, 1556, 1321, 1262, 1256, 1203, 1043, 1015, 955, 866, 776 | 1.01 (3H,s), 1.92 (3H,d,J=2Hz), 6.12 (1H,s), 6.49 (1H,d,J=10Hz), 6.58 (1H,d,J=10Hz) |

TABLE 3

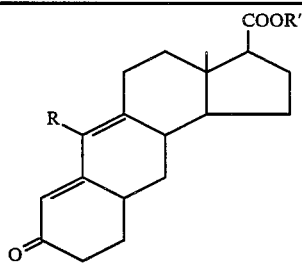

| Compound No | R | R' | Mp. °C. | IR νmax cm$^{-1}$ | NMR δ ppm(CDCl$_3$); UV; or $[\alpha]_D$ |
|---|---|---|---|---|---|
| 7-3 | H | Me | 127~128 | 1733, 1662, 1622, 1585, 1327, 1261, 1238, 1200, 1025, 921, 894 (Nujol) | 0.95 (3H,s), 2.03 (3H,s), 4.66 (1H,t, J=8Hz), 5.74 (1H,s), 6.07 (1H,s) |
| 7-4 | Me | Me | 122~123 | 1734, 1652, 1595, 1570, 1327, 1268, 1235, 1203, 1040, 1022, 875 (Nujol) | 0.93 (3H,s), 1.83 (3H,s), 2.04 (3H,s), 4.62 (1H,dd,J=8 and 7Hz), 6.00 (1H,s) |
| 7-5 | Me | Et | oil | 1727, 1646, 1588, 1574, 1328, 1267, 1182, 1086, 1023, 986, 970 (CHCl$_3$) | 0.93 (3H,s), 1.13 (3H,t,J=7Hz), 1.83 (3H,s), 2.33 (2H,q,J=7Hz), 4.63 (1H,t, J=8Hz), 5.98 (1H,brs) |
| 7-2 | Me | CH$_2$CH$_2$COOH | 190~192 | 1736, 1721, 1630, 1591, 1520, 1306, 1277, 1239, 1208, 1184, | 0.92 (3H,s), 1.82 (3H,s), 2.66 (4H,s), 4.64 (1H,dd,J=8  7Hz), 6.02 (1H, s). |

TABLE 3-continued

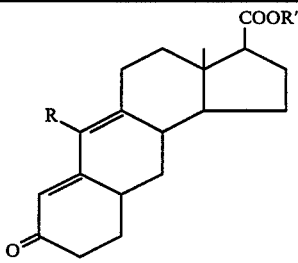

| Compound | | Mp. | IR | |
|---|---|---|---|---|
| No | R | R' | °C. | νmax cm$^{-1}$ | NMR δ ppm(CDCl$_3$); UV; or [α]$_D$ |
| | | | | 1148, 1027, 876, 741 (Nujol) | UV: λ$_{max}^{EtOH}$ 301 nm (ε=29900). [α]$_D$ −201.2 ± 2.4* (C=1.010, CHCl$_3$) |
| 7-6 | Me | CH$_2$CH$_2$CH$_2$CH$_2$COOMe | oil | 1732, 1655, 1587, 1569, 1323, 1260, 1202, 1170, 1140, 1084, 1052, 1022, 1000, 970, 873 (CHCl$_3$) | 0.93 (3H,s), 3.65 (3H,s), 4.61 (1H,t, J=8Hz), 5.98 (1H,s) |

TABLE 4

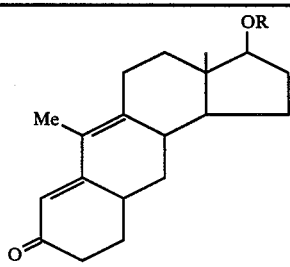

| Compound | Mp. | IR | NMR |
|---|---|---|---|
| No. R | °C. | ν max cm$^{-1}$ | δ ppm (CDCl$_3$) |
| 8-4 Me | oil | 1647, 1590, 1574, 1333, 1273, 1110, 992, 975, 879 (CHCl$_3$) | 0.89(3H, s), 1.83(3H, t, J=1.5Hz), 3.24(1H, t, J=7.5Hz), 3.36(3H, s), 5.99(1H, s) |
| 11-1 Et | oil | 1647, 1588, 1575, 1334, 1272, 1108, 1076, 905, 878 (CHCl$_3$) | 0.88(3H, s), 1.16(3H, t, J=7Hz), 1.82(3H, t, J=1.5Hz), 3.32(1H, t, J=8Hz), 3.83(2H, q, J=7Hz), 5.98(1H, s) |
| 10-2 (cyclopentenyl) | 129~130 | 1639, 1588, 1568, 1235, 1203, 1021, 873, 780, (Nujol) | 0.92(3H, s), 1.85(3H, s), 3.82(1H, t, J=8Hz), 4.30 (1H, brs), 5.84(1H, s) |
| 9-2 (MeO-cyclopentyl) | oil | 1666, 1585, 1575, 1330, 1264, 1203, 1115, 1058, 876 (CCl$_4$) | 0.91(3H, s), 1.83(3H, s), 3.22(3H, s), 3.62(1H, t, J=8Hz), 5.99(1H, s) |
| 11-2 (cyclohexenyl) | 164~166 | 1650, 1585, 1564, 1323, 1178, 1015, 866, 779 (Nujol) | 0.94(3H, s), 1.84(3H, s), 3.82(1H, t, J=8Hz), 4.59 (1H, brs), 5.98(1H, s) |
| 11-3 (diethyl cyclohexenyl) | 126~127.5 | 1662, 1653, 1590, 1568, 1325, 1198, 1186, 870, 785 (Nujol) | 0.77(6H, t, J=7Hz), 0.92(3H, s), 1.83(3H, s), 3.87 (1H, t, J=8Hz), 4.51(1H, t, J=4Hz), 6.00(1H, s) |
| 11-4 (methyl cycloheptenyl) | 141~143 | 1645, 1582, 1563, 1324, 1226, 1160, 1108, 865, 782 (Nujol) | 0.94(3H, s), 1.85(3H, s), 3.74(1H, t, J=8Hz), 4.70 (1H, t, J=7Hz), 5.98(1H, s) |

TABLE 4-continued

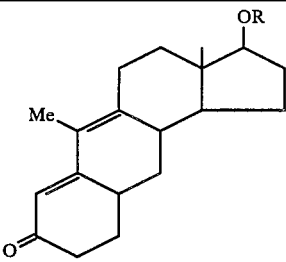

| Compound | | Mp. | IR | NMR |
|---|---|---|---|---|
| No. | R | °C. | $\nu$ max cm$^{-1}$ | $\delta$ ppm (CDCl$_3$) |
| 11-5 | (cyclooctenylmethyl) | 148~150 | 1647, 1587, 1566, 1325, 1264, 1250, 1203, 1160, 1091, 1022, 871 (Nujol) | 0.91(3H, s), 1.83(3H, s), 3.79(1H, t, J=8Hz), 4.38 (1H, t, J=8Hz), 5.82(1H, s), (CCl$_4$) |
| 11-6 | (cyclodecenylmethyl) | 157~159 | 1642, 1585, 1564, 1320, 1228, 1153, 1132, 1088, 862, 823 (Nujol) | 0.94(1H, s), 1.84(3H, s), 3.84(1H, t, J=8Hz), 4.33 (1H, t, J=8Hz), 6.01(1H, s) |

TABLE 5

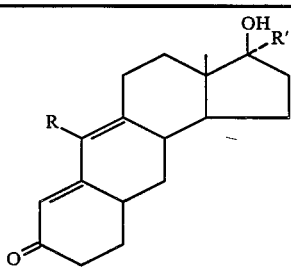

| Compound | | | Mp. | | UV | IR | NMR |
|---|---|---|---|---|---|---|---|
| No. | R | R' | °C. | $[\alpha]_D$ | $\lambda_{max}^{EtOH}$ nm | $\nu_{max}^{Nujol}$ cm$^{-1}$ | $\delta$ ppm (CDCl$_3$) |
| 13-4 | H | —C≡CH | 227~228 | −245.9 ± 5.7° (C = 0.481, CHCl$_3$) | 294 ($\epsilon$ = 30700) | 3334, 3243, 1639, 1613, 1583, 1333, 1307, 1264, 1215, 1061, 1052, 903, 889, 715. | 1.00(3H, s), 2.57(1H, s), 5.77 (1H, s), 6.09(1H, s). |
| 12-3 | Me | Me | 175~177 | −308.1 ± 6.7° (C = 0.519, CHCl$_3$) | 302.5 ($\epsilon$ = 28000) | 3370, 1626, 1583, 1566, 1330, 1268, 1209, 1150, 1102, 1063, 875 | 1.01(3H, s), 1.20(3H, s), 1.83 (3H, s), 5.98(1H, brs) |
| 13-3 | Me | —C≡CH | 170~172 | −232.4 ± 2.7° (C = 1.010, CHCl$_3$) | 302 ($\epsilon$ = 29600) | 3380, 3248, 2104, 1635, 1598, 1572, 1275, 1213, 1094, 1060, 1047, 875, 718 | 0.98(3H, s), 1.84(3H, s), 2.54 (1H, s), 6.00(1H, s) |

TABLE 6

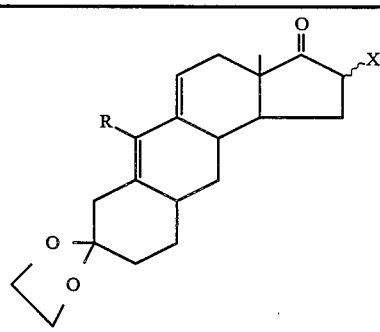

| Compound | | | Mp. | IR | NMR |
|---|---|---|---|---|---|
| No. | R | X | °C. | $\nu$ max cm$^{-1}$ | $\delta$ ppm (CDCl$_3$) |
| 22-1 | H | β-Me | — | — | 0.93(3H, s), 1.01(3H, d, J=7Hz), 3.98(4H, s), 5.42 (1H, brs), 5.90(1H, s) |
| 16-2 | Me | β-Et | 139~141 | 1734, 1132, 1093, 1070, 1053, 1008, 942, | 0.82(3H, s), 0.95(3H, t, J=7Hz), 1.82(3H, s), 3.95 |

TABLE 6-continued

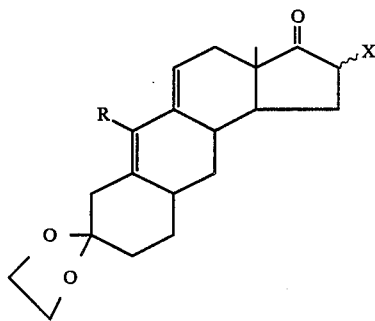

| Compound | | Mp. | IR | NMR |
|---|---|---|---|---|
| No. | R | X | °C. | ν max cm⁻¹ | δ ppm (CDCl$_3$) |
| 20-3 | Me | α-F | 200~202 | 881 (CHCl$_3$) 1758, 1100, 1075, 1058, 1015, 961, 951, 930, 895, 817 (Nujol) | (4H, s), 5.61(1H, brs) 0.91(3H, s), 1.79(3H, s), 3.93(4H, s), 5.07(1H, dd, J=51 and 6.5Hz), 5.61(1H, brs) |
| 21-2 | Me | β-F | 186~188 | 1753, 1246, 1085, 1075, 1046, 963, 945, 890, 820 (Nujol) | 0.99(3H, s), 1.80(3H, s), 3.95(4H, s), 4.75(1H, dt, J=44 and 8.5Hz), 5.60(1H, brs) |
| 22-2 | Me | α-Cl | 136~139 | 1753, 1116, 1096, 1080, 1052, 1030, 947, 818 (Nujol) | 1.01(3H, s), 1.80(3H, s), 3.97(4H, s), 4.06(1H, t, J=8Hz), 5.63(1H, brs) |
| 17-2 | Me | α-Br | 145~150 | — | 0.89(3H, s), 1.79(3H, s), 3.93(4H, s), 4.50(1H, brs), 5.60(1H, brs) |
| 18-2 | Me | β-Br | — | — | 1.04(3H, s), 1.79(3H, s), 3.93(4H, s), 4.16(1H, t, J=12Hz), 5.59(1H, brs) |
| 19-2 | Me | α-OH | — | — | 0.93(3H, s), 1.78(3H, s), 3.83(4H, s), 4.38(1H, dd, J=6 and 3Hz), 5.60(1H, brs) |

TABLE 7

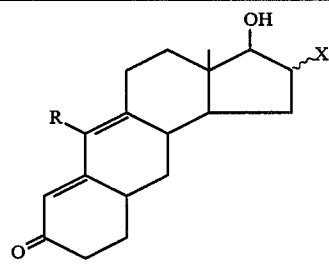

| Compound | | | Mp. | [α]$_D$ | IR ν$_{max}^{Nujol}$ cm⁻¹ | NMR δ ppm (CDCl$_3$) |
|---|---|---|---|---|---|---|
| No. | R | X | °C. | | | |
| 25-1 | H | β-Me | 179~181 | −299.3 ± 11.2° (C = 0.299, CHCl$_3$) | 3606, 3435, 1653, 1616, 1589, 1328, 1257, 1033, 1010, 900 (CHCl$_3$) | 0.93 (3H,s), 1.05 (3H,d,J = 7Hz), 3.68 (1H,d,J = 10Hz), 5.72 (1H,s), 6.03 (1H,s) |
| 23-2 | Me | β-Et | — | −224.1 ± 8.6° (C = 0.307, CHCl$_3$) | 3595, 3435, 1637, 1580, 1563, 1323, 1264, 1087, 1030, 1000, 878 (CHCl$_3$) | 0.89 (3H,s), 0.97 (3H,t), 1.86 (3H,s), 3.69 (1H,brd, J = 9Hz), 5.99 (1H,s) |
| 25-2 | Me | α-F | 152~154 | −304.6 ± 11.2° (C = 0.308, CHCl$_3$) | 3350, 1630, 1582, 1566, 1326, 1265, 1207, 1093, 1057, 1030, 883 | 0.90 (3H,s), 1.83 (3H,s), 3.78 (1H,dd,J = 28.5 and 4.5Hz), 4.97 (1H,ddt,J = 54, 5 and 4.5Hz), 6.01 (1H,brs) |
| 24-5 | Me | β-F | 152~154 | −293.3 ± 6.6° (C = 0.506, CHCl$_3$) | 3385, 1636, 1585, 1578, 1330, 1276, 1218, 1116, 1110, 1090, 1010, 879, 830 | 0.97 (3H,s), 1.84 (3H,s), 3.41 (1H,ddd,J = 21.5, 10, and 6Hz), 4.97 (1H,dddd,J = 56, 10, 7 and 4Hz), 5.99 (1H,s) |
| 25-3 | Me | α-Br | 150~153 (Decmpd) | −147.7 ± 6.3° (C = 0.300, CHCl$_3$) | 3380, 1630, 1578, 1560, 1322, 1258, 1232, 1203, 1088, 870, 725 | 0.91 (3H,s), 1.85 (3H,s), 3.94 (1H,m), 4.19 (1H,dt, J = 8 and 5Hz), 6.03 (1H,s) |
| 25-4 | Me | β-Br | 145~150 (Decmpd) | — | 3425, 1633, 1584, 1560, 1342, 1256, 1235, 1201, 1150, 1097, 995, 870, 728 | 1.03 (3H,s), 1.83 (3H,s), 3.42 (1H,dd,J = 9 and 8Hz), 4.64 (1H,dt,J = 8 and 6Hz), 6.02 (1H,s) |
| 25-5 | Me | α-OH | 206~209 | −269.5 ± 6.0° (C = 0.513, CHCl$_3$) | 3465, 1612, 1564, 1550, 1324, 1265, 1208, 1091, 1060, 965, 873 | 0.90 (3H,s), 1.83 (3H,s), 3.53 (1H,t,J = 5Hz), 4.20 (1H,brs), 6.00 (1H,s) |

TABLE 8

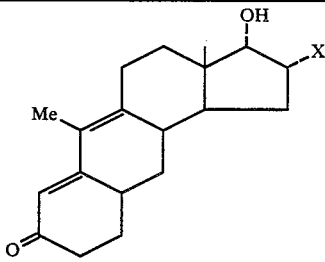

| Compound | | Mp. | | IR | NMR |
|---|---|---|---|---|---|
| No. | X | °C. | $[\alpha]_D$ | $\nu_{max}^{Nujol}$ cm$^{-1}$ | $\delta$ ppm (CDCl$_3$) |
| 25-6 | H | 167.5~168.5 | −315.1 ± 6.9° (C = 0.514, CHCl$_3$) | 3340, 1635, 1591, 1565, 1329, 1207, 1038, 962, 870 | 0.83 (3H,s), 1.86 (3H,d,J = 1.5Hz), 3.79 (1H,d,J = 6Hz), 5.98 (1H,brs) |
| 24-4 | F | 162~164 | −319.0 ±12.0° (C = 0.300, CHCl$_3$) | 3445, 1637, 1588, 1563, 1325, 1203, 1082, 1037, 875, 726 | 0.83 (3H,s), 1.85 (3H,s), 3.87 (1H,dd,J = 5 and 2Hz), 5.30 (1H,dm,J = 53Hz), 6.02 (1H,brs) |
| 25-7 | Cl | 186~188 | −234.5 ± 8.7° (C = 0.316, CHCl$_3$) | 3440, 1630, 1587, 1561, 1322, 1263, 1200, 1093, 1070, 960, 873 | 0.89 (3H,s), 1.83 (3H,s), 3.71 (1H,dd,J = 4.5 and 1.5Hz), 4.64 (1H,dt,J = 9 and 4.5Hz), 6.00 (1H,s) |
| 25-8 | Br | 149~151 | −157.5 ± 6.6° (C = 0.301, CHCl$_3$) | 3320, 1630, 1584, 1560, 1328, 1268, 1210, 1097, 1073, 870 | 0.90 (3H,s), 1.84 (3H,s), 3.68 (1H,dd,J = 4.5 and 1.5Hz), 4.71 (1H,dt,J = 9 and 4.5Hz), 6.01 (1H,s) |

EXAMPLE 27

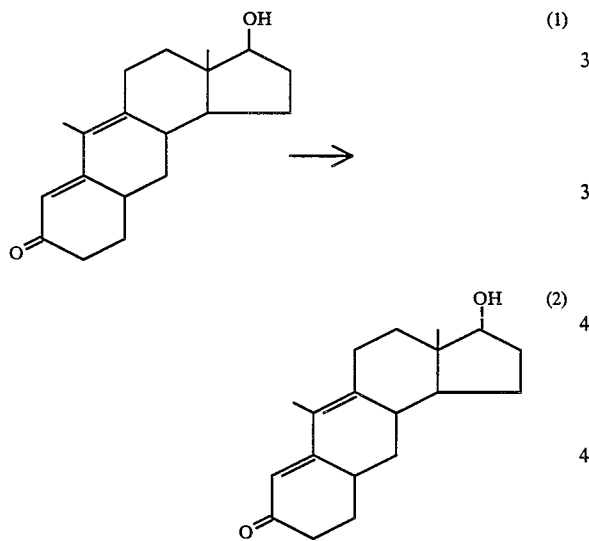

(1) Same as the compound (4) in Example 3
(2) 3α-hydroxy-3aβ,6-dimethyl-2,3,3a,4,5,8,9,10,-10aβ,11,11aβ,11bα-dodecahydro-1H-cyclopenta[a]anthracen-8-one To a solution of 1.00 g of the compound (1) in 20 ml of dry benzene are added 1.10 g of triphenylphosphine and 510 mg of benzoic acid and then 0.66 ml of diethyl azodicarboxylate is added thereto under ice cooling. The mixture is refluxed for 20 minutes. The reaction mixture is placed on the silica gel (25 g) column and eluted with 300 ml of benzene. The solvent is evaporated. To a solution of 1.05 g of the residue in 10 ml of ethanol is added 2 ml of 50% sodium hydroxide solution in a nitrogen atmosphere and the mixture is refluxed for 40 minutes. The reaction mixture, to which is added water is extracted with dichloromethane twice. The extract is washed with water, dried over sodium sulfate, and concentrated under reduced pressure. The residue is chromatographed on silica gel column [Merck, Lobar B, eluted with benzene—ethyl acetate (2:1)] and the resulting crude crystals are recrystallized from acetone to give 370 mg of the compound (2). Colorless prisms, Mp. 167.5° C. to 168.5° C.

Anal. Calcd. (%) for C$_{19}$H$_{26}$O$_2$: C, 79.68; H, 9.15, Found (%): C, 79.64; H, 9.19.

UVλ max(EtOH)nm: 302 ($\epsilon$=28000)

The following are experiments which show results of evaluation for antiandrogenic activity of the compounds prepared in the above mentioned examples.

Experiment 1

Assay for Antiandrogenic Activity (Subcutaneous administration)

(1) Method

The three week-old SD-JCL male rats were castrated and the drug treatment was started from three days after the castration. The rats were divided into groups; one group consists of six rats. One group was intact with any drug, the 2nd group was treated subcutaneously with a solution or suspension of 0.02 mg of testosterone propionate in sesame oil a day, and the other groups was treated with 0.1 to 3 mg of the test compound and 0.02 mg of testosterone propionate in sesame oil a day. This treatment was carried out for 7 days, successively. The rats were killed next day of the last treatment and the seminal vesicles and ventral prostates were taken out and weighed. Antiandrogenic activity of the test compounds were estimated as weight increase of seminal vesicles and ventral prostates induced by testosterone propionate.

(2) Results

The results are summarized in the following Tables 1-1 and 1-2. The test compounds shown in the Table 1-1 significantly inhibit weight increase of seminal vesicles and ventral prostates and are recognized to have a very potent antiandrogenic activity.

TABLE 1-1

| Test Compound | Dosage (Day) | I. R. (%) A* | I. R. (%) B* |
|---|---|---|---|
| (steroid with OH at 17, methyl, 4-en-3-one) | 1 mg | 25 | — |
| (steroid with OH at 17, dienone) | 1 mg | 69 | 44 |
| (steroid with OCOEt, dienone) | 1 mg | 57 | 42 |

TABLE 1-1-continued

| Test Compound | Dosage (Day) | I. R. (%) A* | I. R. (%) B* |
|---|---|---|---|
| (steroid with OH, Me at 17, dienone) | 1 mg | 67 | 41 |
| (steroid with OH at 17, F at 16, dienone) | 1 mg | 77 | 52 |

I. R. means Inhibition rate, A* means seminal vesicle, and B* means prostate.

In addition, the test compounds shown in Table 1-2 also clearly decrease the seminal vesicles and ventral prostates in the weight and the potency is dose dependent. Therefore, the results clearly show that these test compounds have antiandrogenic activity.

TABLE 1-2

| Test Compound | Dosage | Number of Rats | Weight (Mean mg ± S.E.) A* | Weight (Mean mg ± S.E.) B* | I. R. (%) A* | I. R. (%) B* |
|---|---|---|---|---|---|---|
| Control | — | 6 | 6.2 ± 0.3 | 10.6 ± 0.7 | — | — |
| Testosterone propionate | — | 6 | 26.1 ± 0.8 | 40.1 ± 1.3 | — | — |
| Testosterone propionate + (steroid) | 0.1 mg | 6 | 19.9 ± 0.6* | 37.9 ± 3.0 | 31 | — |
| " | 0.3 mg | 5 | 20.7 ± 1.3* | 37.3 ± 3.0 | 27 | — |
| " | 1 mg | 6 | 15.0 ± 0.7* | 27.5 ± 2.2* | 56 | 43 |
| " | 3 mg | 6 | 11.4 ± 0.8* | 23.8 ± 1.6* | 74 | 55 |

*$p < 0.05$

Experiment 2

Assay for Antiandrogenic Activity (Oral Administration)

(1) Method

The three week-old SD-JCL male rats were castrated and the drug treatment was started from three days after the castration. The rats were divided into groups; one group consists of six rats. One group was treated with 0.02 mg of testosterone propionate in sesame oil a day by injecting subcutaneously and the other groups were treated with 0.02 mg of testosterone propionate and simultaneously treated orally with a suspension of 3 mg of the test compound in sesame oil. The castrated control group was treated with sesame oil. This treatment was continued for 7 days, successively. The rats were killed 24 hours after the last treatment and the seminal vesicles and ventral prostates were taken out and weighed.

(2) Results

The results are summarized in the following Tables 2. From the results, these test compound clearly inhibit weight increase of seminal vesicles and ventral prostates by oral administration.

TABLE 2

| Test Compound | I. R. (%) | |
|---|---|---|
| | A* | B* |
| [structure] | 39 | 34 |
| [structure] | 26 | 25 |
| [structure] | 51 | 43 |

The followings show an assay for antiandrogenic activity against androgen-dependent tumor, Shionogi-carcinoma 115 (SC-115). The SC-115 is a tumor cell which grows in the presence of an androgen and its hormone dependency is widely known as a prostatic cancer model. Therefore, the androgenic activity is also estimated by examining the growth inhibition effect against this tumor.

The experiment for estimating the effect againt SC-115 is shown below.

Experiment 3

Assay for growth inhibitory activity against androgen-dependent tumor (Shionogi-carcinoma 115)

(1) Method

The six week-old mice were castrated and 2 ml of Shionogi-carcinoma tumor pieces was grafted into the back subcutaneously on the fifth day from the castration. The grafted mice were divided into groups, each consisting of seven mice, and the drug treatment was started immediately after the graft. One group was intact with any drug, and the 2nd group was treated subcutaneously with 0.1 mg of testosterone propionate a day. The other groups were treated subcutaneously with a suspension of 0.1 mg of testosterone propionate and 0.1 to 2.0 mg per day of test compounds a day as a conventional steroid solution. This treatment was carried out for 14 days, successively. The mice were killed next day of the last treatment and the tumor was taken out to weigh. Tumor growth inhibitory activity of the test compounds were estimated on how much the test compound inhibits the weight increase of tumor induced by testosterone propionate.

(2) Results

As shown in Table 3, these test compounds significantly inhibit the weight increase of the androgen-dependent tumor and the potency is dose dependent. The results clearly show that these test compounds have antiandrogenic activity.

TABLE 3

| Test Compound | Dosage | Number of Mice | Tumor Weight (Mean mg ± S.E.) | Inhibition Rate (%) |
|---|---|---|---|---|
| Control | | 7 | 47 ± 6 | — |
| Testosterone propionate | | 7 | 3241 ± 456 | — |
| Testosterone propionate | | | | |

TABLE 3-continued

| Test Compound | Dosage | Number of Mice | Tumor Weight (Mean mg ± S.E.) | Inhibition Rate (%) |
| --- | --- | --- | --- | --- |
| 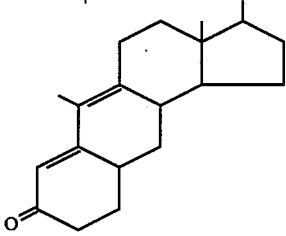 | 0.1 mg<br>0.5 mg<br>2.0 mg | 7<br>7<br>7 | 1682 ± 177*<br>1343 ± 283<br>255 ± 108* | 48<br>59<br>92 |
| Testosterone propionate<br>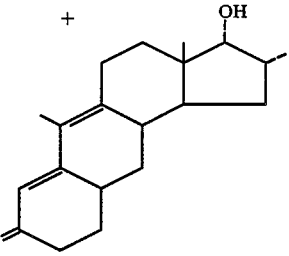 | 0.1 mg<br>0.5 mg<br>2.0 mg | 7<br>7<br>7 | 2871 ± 277<br>1950 ± 144*<br>1004 ± 198** | 11<br>40<br>69 |

*, , * ; p < 0.05, 0.01, 0.001

As shown in the results, the test compounds not only inhibit the weight increase of the prostate and seminal vesicle induced by extrinsic androgen (testosterone propionate) on castrated animals but also inhibit significantly the growth of Shionogi-carcinoma, which depends on androgen. The tumor inhibitory activity of these test compounds is as potent as or much more potent than that of representative antiandrogen such as chlormadinone or cyproterone in the comparative experiment.

Moreover on the mature animals, the test compounds significantly decrease the weight of the prostate and seminal vesicle against intrinsic androgen. No other activity such as androgenic, estrogenic, antiestrogenic, and progensterone activity are recognized.

Accordingly, it is expected that the compounds (I) of the present invention are effectively applied to the treatment of not only prostatomegaly but also the treatment of prostatic cancer.

What we claim is:

1. A substituted anthrasteroid derivative represented by the following formula:

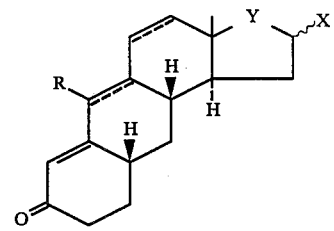

wherein R is hydrogen or lower alkyl; X is hydrogen, lower alkyl, halogen, hydroxy, hydroxymethyl, or halomethyl; Y is C=O, CH~OR', or OH C ... R", wherein R' is (1) hydrogen, (2) lower alkyl, (3) saturated or unsaturated cycloalkyl optionally substituted by ethyl, methoxy, or ethoxy, or (4) aliphatic lower acyl which may have carboxy or its lower alkyl ester at the terminal; R" is lower alkyl or lower alkynyl; the dotted line indicates the presence or absence of a double bond; and the wavy line indicates an α or β configuration with the proviso that in the absence of a double bond between 5a and 6 positions, the configuration of the hydrogen atom at the 5a position is α; or an ethylene acetal derivative thereof.

2. A compound claimed in claim 1, wherein R is methyl.

3. A compound claimed in claim 1, wherein X is hydrogen.

4. A compound claimed in claim 1, wherein Y is CH—OH.

5. A compound claimed in claim 1, wherein Y is C=O.

6. A compound claimed in claim 1, namely, 3β-hydroxy-3aβ,6-dimethyl-2,3,3a,4,5,8,9,10,10aβ,11,-11aβ,11bα-dodecahydro-1H-cyclopenta[a]anthracen-8-one.

7. A compound claimed in claim 1, namely 3aβ,6-dimethyl-2,3,3a,4,5,8,9,10,10aβ,11,11aβ,11bα-dodecahydro-1H-cyclopenta[a]anthracene-3,8-dione.

* * * * *